United States Patent
Vautravers et al.

(10) Patent No.: US 10,202,324 B2
(45) Date of Patent: Feb. 12, 2019

(54) PROCESS FOR THE PREPARATION OF MELONAL

(71) Applicant: BASF SE, Ludwigshafen (DE)

(72) Inventors: Nicolas Vautravers, Mannheim (DE); Joaquim Henrique Teles, Waldsee (DE); Ralf Pelzer, Fürstenberg (DE); Daniel Schneider, Frankenthal (DE); Florian Garlichs, Neustadt (DE); Andreas Keller, Speyer (DE); Andrei-Nicolae Parvulescu, Ruppertsberg (DE); Ulrich Müller, Neustadt (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 15/571,107

(22) PCT Filed: May 4, 2016

(86) PCT No.: PCT/EP2016/060062
§ 371 (c)(1),
(2) Date: Nov. 1, 2017

(87) PCT Pub. No.: WO2016/177814
PCT Pub. Date: Nov. 10, 2016

(65) Prior Publication Data
US 2018/0170850 A1    Jun. 21, 2018

(30) Foreign Application Priority Data

May 4, 2015    (EP) .................................... 15166260

(51) Int. Cl.
| | | |
|---|---|---|
| *C07C 45/54* | (2006.01) | |
| *C07C 45/78* | (2006.01) | |
| *C07C 67/39* | (2006.01) | |
| *C07C 45/64* | (2006.01) | |

(52) U.S. Cl.
CPC .............. *C07C 45/54* (2013.01); *C07C 45/64* (2013.01); *C07C 45/78* (2013.01); *C07C 67/39* (2013.01)

(58) Field of Classification Search
CPC .......... C07C 45/54; C07C 45/64; C07C 45/78
See application file for complete search history.

(56) References Cited

U.S. PATENT DOCUMENTS

| | | |
|---|---|---|
| 9,171,568 B1 | 10/2015 | Nicholls et al. |
| 9,446,390 B2 | 9/2016 | Parvulescu et al. |
| 9,464,029 B2 | 10/2016 | Boehling et al. |
| 9,518,211 B2 | 12/2016 | Kimura et al. |
| 9,540,305 B2 | 1/2017 | Parvulescu et al. |
| 9,561,995 B2 | 2/2017 | Maurer et al. |
| 9,640,839 B2 | 5/2017 | Porta Garcia et al. |
| 9,688,648 B2 | 6/2017 | Teles et al. |
| 9,695,099 B2 | 7/2017 | Liu et al. |
| 9,725,428 B2 | 8/2017 | Teles et al. |
| 9,738,616 B2 | 8/2017 | Riedel et al. |
| 9,758,504 B2 | 9/2017 | Dehn et al. |
| 9,765,001 B2 | 9/2017 | Rudenauer et al. |
| 9,765,003 B2 | 9/2017 | Vautravers et al. |
| 9,793,577 B2 | 10/2017 | Porta Garcia et al. |
| 9,796,654 B2 | 10/2017 | Vautravers et al. |
| 9,856,199 B2 | 1/2018 | Hickmann et al. |
| 9,878,965 B2 | 1/2018 | Spannhoff et al. |
| 2014/0047837 A1 | 2/2014 | Wortmann et al. |
| 2014/0357718 A1 | 12/2014 | Feuerstein et al. |
| 2015/0090226 A1 | 4/2015 | Dolan et al. |
| 2015/0090231 A1 | 4/2015 | Dolan et al. |
| 2015/0090344 A1 | 4/2015 | Dolan et al. |
| 2015/0090610 A1 | 4/2015 | Dolan et al. |
| 2015/0090611 A1 | 4/2015 | Dolan et al. |
| 2015/0094202 A1 | 4/2015 | Dolan et al. |
| 2016/0109067 A1 | 4/2016 | Kimura et al. |
| 2016/0122296 A1 | 5/2016 | Parvulescu et al. |
| 2016/0185762 A1 | 6/2016 | Teles et al. |
| 2016/0186932 A1 | 6/2016 | Weickert et al. |
| 2016/0201853 A1 | 7/2016 | Weickert et al. |
| 2016/0201854 A1 | 7/2016 | Weickert et al. |
| 2016/0250624 A1 | 9/2016 | Parvulescu et al. |
| 2016/0256859 A1 | 9/2016 | Parvulescu et al. |
| 2016/0264543 A1 | 9/2016 | Vautravers et al. |
| 2016/0279621 A1 | 9/2016 | Parvulescu et al. |
| 2016/0312149 A1 | 10/2016 | Vautravers et al. |
| 2016/0318860 A1 | 11/2016 | Vautravers et al. |
| 2016/0325228 A1 | 11/2016 | Feyen et al. |
| 2016/0332152 A1 | 11/2016 | Parvulescu et al. |
| 2016/0368843 A1 | 12/2016 | Teles et al. |
| 2017/0037021 A1 | 2/2017 | Stork et al. |

(Continued)

FOREIGN PATENT DOCUMENTS

| | | | |
|---|---|---|---|
| WO | WO-2014068134 A2 | 5/2014 | |
| WO | WO-2014199348 A2 | 12/2014 | |

(Continued)

OTHER PUBLICATIONS

U.S. Appl. No. 61/684,162, filed Aug. 17, 2012.
U.S. Appl. No. 61/841,946.
U.S. Appl. No. 15/676,398, filed Aug. 14, 2017.
U.S. Appl. No. 61/841,954.
U.S. Appl. No. 61/830,182, filed Jun. 3, 2013.
U.S. Appl. No. 61/756,614.
U.S. Appl. No. 61/841,942.
U.S. Appl. No. 61/939,889.
U.S. Appl. No. 61/939,895.
U.S. Appl. No. 61/939,896.

(Continued)

*Primary Examiner* — Sikarl A Witherspoon
(74) *Attorney, Agent, or Firm* — Drinker Biddle & Reath LLP

(57) ABSTRACT

A process for preparing 2,6-dimethyl-5-heptenal, comprising oxidizing citral of which more than 50% are present as geranial with hydrogen peroxide in the presence of a catalyst comprising a Baeyer-Villiger oxidation catalyst, preferably a tin-containing molecular sieve.

18 Claims, No Drawings

(56) References Cited

U.S. PATENT DOCUMENTS

| | | |
|---|---|---|
| 2017/0037296 A1 | 2/2017 | Kimura et al. |
| 2017/0044421 A1 | 2/2017 | Parvulescu et al. |
| 2017/0197830 A1 | 7/2017 | Riedel et al. |
| 2017/0225959 A1 | 8/2017 | Maurer et al. |
| 2017/0233780 A1 | 8/2017 | Breuer et al. |
| 2017/0233874 A1 | 8/2017 | Aust et al. |
| 2017/0246620 A1 | 8/2017 | Parvulescu et al. |
| 2017/0275076 A1 | 9/2017 | Edgington et al. |
| 2017/0275225 A1 | 9/2017 | Riedel et al. |
| 2017/0283352 A1 | 10/2017 | Fenlon et al. |
| 2017/0292084 A1 | 10/2017 | Stork et al. |
| 2017/0298034 A1 | 10/2017 | Riedel et al. |
| 2017/0320847 A1 | 11/2017 | Vautravers et al. |
| 2017/0334820 A1 | 11/2017 | Pelzer et al. |
| 2017/0334824 A1 | 11/2017 | Pelzer et al. |
| 2017/0336030 A1 | 11/2017 | Weickert et al. |
| 2017/0355670 A1 | 12/2017 | Rudenauer et al. |
| 2017/0362532 A1 | 12/2017 | Pelzer et al. |
| 2018/0002266 A1 | 1/2018 | Bru Roig et al. |
| 2018/0022611 A1 | 1/2018 | Feyen et al. |

FOREIGN PATENT DOCUMENTS

| | | |
|---|---|---|
| WO | WO-2014199349 A2 | 12/2014 |
| WO | WO-2015018807 A2 | 2/2015 |
| WO | WO-2015018815 A1 | 2/2015 |
| WO | WO-2015022623 A2 | 2/2015 |
| WO | WO-2015025268 A1 | 2/2015 |
| WO | WO-2015032851 A2 | 3/2015 |
| WO | WO-2015059175 A1 | 4/2015 |
| WO | WO-2015083113 A1 | 6/2015 |
| WO | WO-2015123530 A1 | 8/2015 |
| WO | WO-2015123531 A1 | 8/2015 |
| WO | WO-2015144695 A1 | 10/2015 |
| WO | WO-2015169939 A1 | 11/2015 |
| WO | WO-2015181283 A1 | 12/2015 |
| WO | WO-2015185625 A2 | 12/2015 |
| WO | WO-2015185633 A1 | 12/2015 |
| WO | WO-2015197699 A1 | 12/2015 |
| WO | WO-2016024201 A1 | 2/2016 |
| WO | WO-2016/038192 A1 | 3/2016 |
| WO | WO-2016/050836 A1 | 4/2016 |
| WO | WO-2016066629 A1 | 5/2016 |
| WO | WO-2016074918 A1 | 5/2016 |
| WO | WO-2016075100 A1 | 5/2016 |
| WO | WO-2016075129 A1 | 5/2016 |
| WO | WO-2016097239 A1 | 6/2016 |
| WO | WO-2016097242 A1 | 6/2016 |
| WO | WO-2016/116406 A1 | 7/2016 |
| WO | WO-2016128538 A1 | 8/2016 |
| WO | WO-2016/135133 A1 | 9/2016 |
| WO | WO-2016139338 A1 | 9/2016 |
| WO | WO-2016142503 A1 | 9/2016 |
| WO | WO-2016177814 A1 | 11/2016 |

OTHER PUBLICATIONS

U.S. Appl. No. 61/990,490.
U.S. Appl. No. 62/081,243, filed Nov. 18, 2014.
U.S. Appl. No. 62/005,011, filed May 30, 2014.
U.S. Appl. No. 61/990,773.
U.S. Appl. No. 62/046,667.
Baerlocher, C., et al., Atlas of Zeolite Framework Types, Sixth Revised Edition, Elsevier, Amsterdam, the Netherlands, 2007, pp. 72-73.
Corma, A., et al., "A new, alternative, halogen-free synthesis for the fragrance compound Melonal using zeolites and mesoporous materials as oxidation catalysts", Journal of Catalysis, vol. 234, No. 1, (2005), pp. 96-100.
International Search Report for PCT/EP2016/060062 dated Jun. 17, 2016.
Sing, K.S.W., et al., "Reporting Physisorption Data for Gas/Solid Systems with Special Reference to the Determination of Surface Area and Porosity (Recomendations 1984)", Pure and Applied Chemistry, vol. 57, No. 4, (1985), pp. 603-619.
Written Opinion of the International Searching Authority for PCT/EP2016/060062 dated Jun. 17, 2016.

PROCESS FOR THE PREPARATION OF MELONAL

CROSS-REFERENCE TO RELATED APPLICATIONS

This application is a national stage application (under 35 U.S.C. § 371) of PCT/EP2016/060062, filed May 4, 2016, which claims benefit of European Application No. 15166260.8, filed May 4, 2015, both of which are incorporated herein by reference in their entirety.

The present invention relates to a process for the oxidation of citral, in particular a Baeyer-Villiger-type oxidation of citral with hydrogen peroxide, in the presence of a catalyst comprising a tin-containing molecular sieve as catalyst for the Baeyer-Villiger oxidation.

Oxidation reactions of organic compounds and in particular the Baeyer-Villiger reaction is of considerable interest in order to convert readily available carbonyl compounds in more complex and valuable products.

The chemoselective oxidation of citral (3,7-dimethylocta-2,6-dienal) with hydrogen peroxide and tin-containing porous material was developed is described in Corma et al., Journal of Catalysis 234 (2005) 96-100. It is noted that the synthesis of the catalyst is very complex, illustrated, for example, by the long synthesis time, the necessity to employ crystallization auxiliaries such as HF, costly templating agents, and the like, all of which rendering the scale-up difficult. Further, in particular, it is explicitly stated in Corma et al. that the citral used for carrying out the experiments was a commercial product, in particular a product bought from Aldrich. It is noted that all citral products offered by Aldrich are 1:1 mixture of geranial (trans-citral; the E-isomer of citral) und neral (ds-citral; the Z-isomer of citral). Consequently, irrespective which formula is shown in the document, the direct and unambiguous teaching of Corma et al. for the person skilled in the art is unequivocally restricted to a 1:1 mixture of geranial und neral only, and every formula is interpreted by the skilled person as representing said 1:1 mixture of geranial und neral.

WO 2014/068134 describes the oxidation of citral with hydrogen peroxide and a tin-containing zeolitic material as catalyst. A 1:1 mixture of geranial (fans-citral) und neral (cis-citral) is used as the citral starting material.

Since the Baeyer-Villiger oxidation product obtained from the oxidation of citral, 2,6-dimethyl-5-heptenal (also known as melonal), is a commercially interesting product, there is a constant need for improving the preparation process. In particular, there is a constant need for providing processes with exhibit a high selectivity. Further, the reaction time is of interest in industrial-scale processes.

Thus, it was an object of the present invention to provide a process for the Baeyer-Villiger oxidation of citral with hydrogen peroxide which does not exhibit the disadvantages of the methods according to the prior art and wherein a high selectivity to the product of the Baeyer-Villiger oxidation is achieved.

It was a further object of the present invention to provide a process for the Baeyer-Villiger oxidation of citral with hydrogen peroxide which does not exhibit the disadvantages of the methods according to the prior art and wherein a short reaction time ca be realized.

Surprisingly, it was found that if as starting material, a citral is employed which contains more than 50% of the trans-citral, i.e. geranial, the above-mentioned objections can be solved.

Therefore, the present invention relates to a process, preferably a liquid-phase process, for preparing a compound of formula (III)

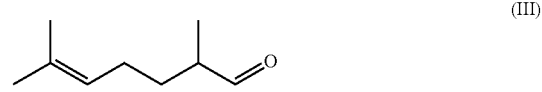

(III)

said process comprising
(i) oxidizing a compound of formula (I)

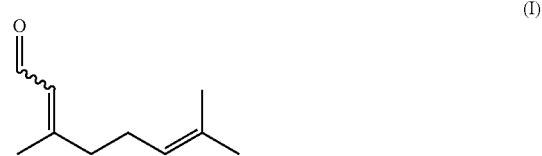

(I)

of which more than 50% are present as compound of formula (Ia)

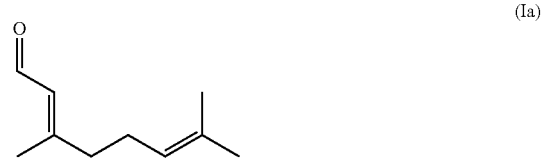

(Ia)

with hydrogen peroxide in the presence of a catalyst comprising a tin-containing molecular sieve, obtaining a reaction mixture comprising a compound of formula (II)

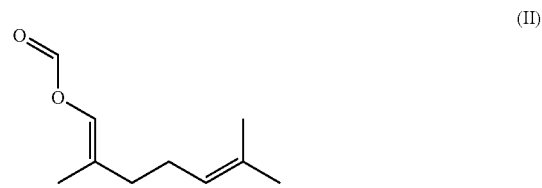

(II)

and optionally the compound of formula (III).

Process

Commercially available citral is a mixture of geranial and neral with a molar ratio of 1:1. According to the present invention, the compound of formula (I) is employed comprising more than 50% of the trans isomer, i.e. more than 50% of the compound of formula (I) are present as compound of formula (Ia), and less than 50% are present as compound of formula (Ib)

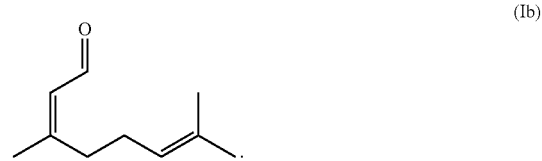

(Ib)

These mixtures comprising more than 50% of the compound of formula (I) as compound of formula (Ia) can be prepared according to any conceivable methods wherein distilling, such as fractional distilling, a 1:1 mixture of geranial and neral may be preferred.

According to (i), it is preferred that at least 55%, more preferably at least 60%, more preferably at least 65%, more preferably at least 70%, more preferably at least 75%, more preferably at least 80%, more preferably at least 85%, more preferably at least 90% of the compound of formula (I) are present as compound of formula (Ia). More preferably, at least 95%, more preferably at least 96%, more preferably at least 97%, more preferably at least 98% of the compound of formula (I) are present as compound of formula (Ia). Therefore, it is preferred that at least 98% the compound of formula (I) employed in (i) consist of the compound of formula (Ia) and at most 2% the compound of formula (I) employed in (i) consist of the compound of formula (Ib). According to conceivable embodiments, at least 99% the compound of formula (I) employed in (i) consist of the compound of formula (Ia) and at most 1% the compound of formula (I) employed in (i) consist of the compound of formula (Ib), or at least 99.5% the compound of formula (I) employed in (i) consist of the compound of formula (Ia) and at most 0.5% the compound of formula (I) employed in (i) consist of the compound of formula (Ib), or at least 99.9% the compound of formula (I) employed in (i) consist of the compound of formula (Ia) and at most 0.01% the compound of formula (I) employed in (i) consist of the compound of formula (Ib).

As Baeyer-Villiger oxidation catalyst, a tin-containing molecular sieve is preferably employed. Regarding the chemical composition and physical characteristics such as BET specific surface area, pore volume, pore volume distribution, channels, crystallinity, and the like, no specific restrictions exist provided that the process of the invention can be carried out. Preferably, the tin-containing molecular sieve comprises micropores, or mesopores, or micropores and mesopores. In addition to the micropores and/or mesopores, the tin-containing molecular sieve may also comprise macropores. In the context of the present invention, the term "micropores" relates to pores having a diameter of less than 2 nm, the term "mesopores" relates to pores having a diameter of from 2 to 50 nanometer, and the term "macropores" relates to pores having a diameter of greater than 50 nanometer.

In case the tin-containing molecular sieve comprises or consists of a mesoporous molecular sieve, it is preferred that the tin-containing molecular sieve exhibits a type IV $N_2$ adsorption isotherm as defined, for example, in K. S. W. Sing, D. H. Everett, R. A. W. Haul, L. Moscou, R. A. Pierotti, J. Rouquerol, T. Siemieniewska, Reporting Physisorption Data for Gas/Solid Systems with Special Reference to the Determination of Surface Area and Porosity (Recommendations 1984) Pure & Appl. Chem. 57 (1985) 603-619. In case the tin-containing molecular sieve comprises or consists of a mesoporous molecular sieve, it may be preferred that the tin-containing molecular sieve comprises, preferably consists of, MCM-41.

Preferably, the tin-containing molecular sieve comprises, preferably consists of, a microporous molecular sieve. Such a microporous molecular sieve may comprise, for example, a tin-containing metal organic framework (MOF) material or a tin-containing zeolitic material. More preferable, the tin-containing molecular sieve comprises, preferably consists of, a tin-containing zeolitic material.

The framework structure type of the tin-containing zeolitic material is not subject to any specific restrictions, provided that the process of the invention can be carried out. Generally, the framework structure type of the tin-containing zeolitic material may be selected from the group consisting of ABW, ACO, AEI, AEL, AEN, AET, AFG, AFI, AFN, AFO, AFR, AFS, AFT, AFV, AFX, AFY, AHT, ANA, APC, APD, AST, ASV, ATN, ATO, ATS, ATT, ATV, AVL, AWO, AWW, BCT, BEA, BEC, BIK, BOF, BOG, BOZ, BPH, BRE, BSV, CAN, CAS, CDO, CFI, CGF, CGS, CHA, CHI, CLO, CON, CZP, DAC, DDR, DFO, DFT, DOH, DON, EAB, EDI, EEI, EMT, EON, EPI, ERI, ESV, ETR, EUO, EZT, FAR, FAU, FER, FRA, GIS, GIU, GME, GON, GOO, HEU, IFO, IFR, IFW, IFY, IHW, IMF, IRN, IRR, ITY, ISV, ITE, ITG, ITH, ITN, ITR, ITT, ITV, ITW, IWR, IWS, IWV, IWW, JBW, JOZ, JRY, JSN, JSR, JST, JSW, KFI, LAU, LEV, LIO, LIT, LOS, LOV, LTA, LTF, LTJ, LTL, LTN, MAR, MAZ, MEI, MEL, MEP, MER, MFI, MFS, MON, MOR, MOZ, MRE, MSE, MSO, MTF, MTN, MTT, MTW, MVY, MWW, NAB, NAT, NES, NON, NPO, NPT, NSI, OBW, OFF, OKO, OSI, OSO, OWE, PAR, PAU, PCR, PHI, PON, PUN, RHO, RON, RRO, RSN, RTE, RTH, RUT, RWR, RWY, SAF, SAO, SAS, SAT, SAV, SBE, SBN, SBS, SBT, SEW, SFE, SFF, SFG, SFH, SFN, SFO, SFS, SFV, SFW, SGT, SIV, SOD, SOF, SOS, SSF, SSO, SSY, STF, STI, STT, STW, SVR, SW, SZR, TER, THO, TON, TSC, TUN, UEI, UFI, UOS, UOV, UOZ, USI, UTL, UWY, VET, VFI, VNI, VSV, WEI, WEN, YUG, ZON, mixtures of two or more thereof, and mixed types of two or more thereof.

Preferably, the framework structure type of the tin-containing zeolitic material is selected from the group consisting of BEA, MWW, MFI, mixtures of two or more thereof, and mixed types of two or more thereof. More preferably, the framework structure type of the tin-containing zeolitic material is selected from the group consisting of BEA, MWW, mixtures thereof, and mixed types thereof. More preferably, the framework structure type of the tin-containing zeolitic material comprises, more preferably consists of, the structure type BEA. With regard to the definition of the framework structures, in particular the framework structure type BEA, reference is made to the respective definition in Baerlocher at al., Atlas of Zeolite Framework Structures, Sixth Revised Edition, Elsevier, Amsterdam (2007), in particular pp 72-73.

Therefore, the present invention relates to the process as defined above, comprising
(i) oxidizing a compound of formula (I) of which more than 50% are present as compound of formula (Ia)

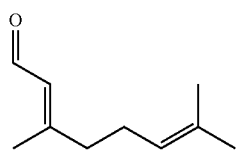

(Ia)

with hydrogen peroxide in the presence of a catalyst comprising a tin-containing zeolitic material of framework structure type BEA, obtaining a reaction mixture comprising a compound of formula (II) and optionally the compound of formula (III).

Preferably, at least 90 weight-%, more preferably at least 95 weight-%, more preferably at least 97 weight-%, more preferably at least 98 weight-% of the framework structure of the tin-containing molecular sieve consist of Sn, O, H, a tetravalent element Y, and optionally a trivalent element X. More preferably, at least 99 weight-%, more preferably at least 99.5 weight-%, more preferably at least 99.9 weight-% of the framework structure of the tin-containing molecular sieve consist of Sn, O, H, a tetravalent element Y, and optionally a trivalent element X.

With respect to the tetravalent element Y the presence of which in the framework of the molecular sieve is also referred to as the presence of $YO_2$, no specific restrictions exist. Preferably, Y comprises, more preferably is, one or more of Si, Ge, Ti, and Zr. More preferably, Y comprises, more preferably is, Si. With respect to the trivalent element X the presence of which in the framework of the molecular sieve is also referred to as the presence of $X_2O_3$, no specific restrictions exist. Preferably, X is not Al. Preferably, X comprises, more preferably is, one or more of B, In, Ga, and Fe. More preferably, Y comprises, more preferably is, B. Preferably, the tin-containing molecular sieve is free of Al wherein the term "free of Al" refers to a chemical composition of the tin-containing molecular sieve which comprises Al only in traces which are present due to impurities of the starting materials from which the tin-containing molecular sieve is prepared or due to incomplete removal of Al from a Al containing molecular sieve which is used for preparing the tin-containing molecular sieve.

With regard to the tin content of the tin-containing molecular sieve, it is preferred that this content is in the range of from 0.1 to 20 weight-%, more preferably in the range of from 0.5 to 18 weight-%, more preferably in the range of from 0.75 to 17 weight-%, more preferably in the range of from 1 to 16 weight-%, more preferably in the range of from 1.5 to 15 weight-%, more preferably in the range of from 2 to 14 weight-%. Preferred ranges are, for example, 8 to 14 weight-%, more preferably 10 to 14 weight-%.

Therefore, the present invention also relates to the process as defined above, comprising
(i) oxidizing a compound of formula (I) of which more than 50% are present as compound of formula (Ia)

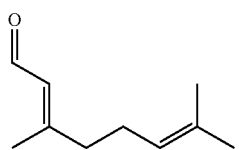

(Ia)

with hydrogen peroxide in the presence of a catalyst comprising a tin-containing zeolitic material of framework structure type BEA having a tin content in the range of from 2 to 14 weight-% based on the total weight of the tin-containing molecular zeolitic material, obtaining a reaction mixture.

Preferably, at least 90 weight-%, more preferably at least 95 weight-%, more preferably at least 97 weight-%, more preferably at least 98 weight-% of the framework structure of the tin-containing zeolitic material of framework structure type BEA consist of Sn, O, H, Si, and optionally B. More preferably, at least 99 weight-%, more preferably at least 99.5 weight-%, more preferably at least 99.9 weight-% of the framework structure of the tin-containing zeolitic material of framework structure type BEA consist of Sn, O, H, Si, and optionally B.

Preferably, in the framework structure of the tin-containing molecular sieve, preferably of the tin-containing zeolitic material, more preferably of the tin-containing zeolitic material of framework structure type BEA, the molar ratio $B_2O_3:SiO_2$ is at most 0.01:1, preferably in the range of from 0.001:1 to 0.01:1, more preferably in the range of from 0.001:1 to 0.003:1.

Therefore, the present invention also relates to the process as defined above, comprising
(i) oxidizing a compound of formula (I) of which more than 50% are present as compound of formula (Ia)

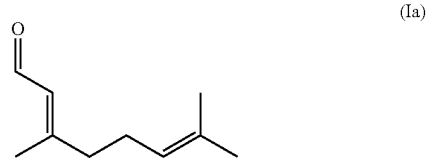

(Ia)

with hydrogen peroxide in the presence of a catalyst comprising a tin-containing zeolitic material of framework structure type BEA having a tin content In the range of from 2 to 14 weight-% based on the total weight of the tin-containing molecular zeolitic material, wherein at least 99 weight-% of the framework structure of the tin-containing zeolitic material of framework structure type BEA consist of Sn, O, H. Si, and optionally B, obtaining a reaction mixture.

Therefore, the present invention also relates to the process as defined above, comprising
(i) oxidizing a compound of formula (I) of which more than 50% are present as compound of formula (Ia)

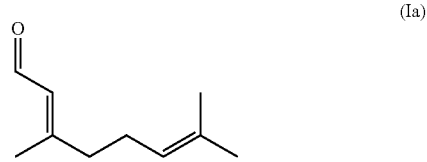

(Ia)

with hydrogen peroxide in the presence of a catalyst comprising a tin-containing zeolitic material of framework structure type BEA having a tin content in the range of from 2 to 14 weight-% based on the total weight of the tin-containing molecular zeolitic material, wherein at least 99 weight-% of the framework structure of the tin-containing zeolitic material of framework structure type BEA consist of Sn, O, H, Si, and B, wherein in the framework structure of the tin-containing zeolitic material of framework structure type BEA, the molar ratio $B_2O_3:SiO_2$ is in the range of from 0.001:1 to 0.01:1, obtaining a reaction mixture.

With regard to the preparation process according to which the tin-containing molecular sieve, preferably the tin-containing zeolitic material, more preferably the tin-containing zeolitic material of framework structure type BEA can be prepared, no specific restrictions exist. In particular with regard to the tin-containing zeolitic material of framework structure type BEA, it is preferred that the preparation process of the zeolitic material comprises incorporating the tin into a suitable zeolitic material starting material by a solid-state ion-exchange method. Such a suitable zeolitic material starting material may be, for example, a zeolitic material having vacant tetrahedral framework sites in which sites the tin is incorporated, preferably by a solid-state ion-exchange method.

A preferred process for preparing the tin-containing zeolitic material having a BEA framework structure and a preferred tin-containing zeolitic material having a BEA framework structure are described hereinunder by the following embodiments and combinations of embodiments according to the dependencies and references as indicated:

1. A process for preparing a tin-containing zeolitic material having a BEA framework structure comprising
   (a) providing a zeolitic material having a BEA framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said BEA framework structure having vacant tetrahedral framework sites;
   (b) providing a tin-on source in solid form;
   (c) incorporating tin into the zeolitic material provided in (a) by bringing the zeolitic material provided in (a) in contact with the tin-ion source provided in (b) under solid-state ion exchange conditions, obtaining a tin-containing zeolitic material having a BEA framework structure;
   (d) subjecting the zeolitic material obtained from (c) to a heat treatment;
   (e) optionally treating the heat-treated zeolitic material obtained from (d) with an aqueous solution having a pH of at most 5.
2. The process of embodiment 1, wherein Y is Si and X is B.
3. The process of embodiment 1 or 2, wherein according to (a), the zeolitic material having a BEA framework structure having vacant tetrahedral framework sites is provided by a method comprising
   (a.1) providing a zeolitic starting material having a BEA framework structure, wherein the framework structure of the zeolitic starting material comprises $X_2O_3$ and $YO_2$ and the molar ratio $X_2O_3$:$YO_2$ is greater than 0.02:1, preferably at least 0.03:1, more preferably in the range of from 0.03:1 to 0.07:1, more preferably from 0.03:1 to 0.06:1, more preferably from 0.03:1 to 0.05:1;
   (a.2) creating vacant tetrahedral framework sites by treating the zeolitic starting material provided in (a.1) with a liquid solvent system, preferably under reflux, obtaining a zeolitic material having a molar ratio $X_2O_3$:$YO_2$ of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., preferably for a period in the range of from 6 to 20 h, more preferably from 7 to 17 h, more preferably from 8 to 12 h;
   (a.3) at least partially separating the zeolitic material obtained from (a.2) from the liquid solvent system, optionally including drying;
   (a.4) optionally calcining the separated zeolitic material obtained from (a.3), preferably at a temperature in the range of from 400 to 700° C., more preferably from 450 to 550° C., and preferably for a time period in the range of from 1 to 10 h, more preferably from 3 to 6 h.
4. The process of any of embodiments 1 to 3, wherein in the framework structure of the zeolitic material provided in (a), the molar ratio $X_2O_3$:$YO_2$ is at most 0.02:1, preferably at most 0.01:1, more preferably in the range of from 0.0005:1 to 0.01:1, more preferably from 0.0009:1 to 0.003:1.
5. The process of any of embodiments 1 to 4, wherein at least 95 weight-%, preferably at least 98 weight-%, more preferably at least 99 weight-% of the framework structure of the zeolitic material provided in (a) consist of $X_2O_3$ and $YO_2$.
6. The process of any of embodiments 1 to 5, wherein the tin-ion source provided in (b) is selected from the group consisting of tin(II) alkoxides, tin(IV) alkoxides, tin(II) salts of organic acids, tin(IV) salts of organic acids, and a mixture a two or more thereof, preferably from the group consisting of tin(II) alkoxides having from 1 to 4 carbon atoms, tin(IV) alkoxides having from 1 to 4 carbon atoms, tin(II) salts of organic acids having from 1 to 6, tin(IV) salts of organic acids having from 1 to 6 carbon atoms, and a mixture a two or more thereof, wherein more preferably, the tin-ion source provided in (ii) is tin(II) acetate.
7. The process of any of embodiments 1 to 6, wherein according to (c), the molar ratio of tin contained in the tin-ion source brought into contact with zeolitic material relative to the vacant tetrahedral framework sites of the zeolitic material is at most 1:1.
8. The process of any of embodiments 1 to 7, wherein in (c), bringing the zeolitic material provided in (a) in contact with the tin-ion source provided in (b) under solid-state ion exchange conditions comprises mixing the zeolitic material provided in (a) with the tin-ion source.
9. The process of embodiment 8, wherein in (c), the zeolitic material is mixed with the tin-ion source for a time period in the range of from 2 min to 5 h, preferably from 5 min to 3 h, more preferably from 10 min to 2 h.
10. The process of embodiment 8 or 9, wherein the mixing is carried out under stirring at a stirring energy input min the range of from 100 to 1000 W, preferably from 200 to 800 W, more preferably from 300 to 600 W.
11. The process of any of embodiments 8 to 10, comprising grinding and/or milling the zeolitic material prior to milling the zeolitic material together with the tin-ion source, or grinding and/or milling the tin-ion source prior to milling the zeolitic material together with the tin-ion source, or grinding and/or milling the zeolitic material prior to milling the zeolitic material together with the tin-ion source and grinding and/or milling the tin-ion source prior to milling the zeolitic material together with the tin-ion source.
12. The process of any of embodiments 8 to 10, comprising kneading the zeolitic material and the tin-ion source, optionally in the form of a suspension.
13. The process of any of embodiments 1 to 11, wherein the heat-treating according to (d) comprises calcining, wherein the calcining is preferably carried out at a temperature in the range of from 400 to 700° C., more preferably from 450 to 650° C., more preferably from 500 to 600° C., preferably for a time period in the range of from 1 to 10 h, more preferably from 2 to 8 h, more preferably from 3 to 6 hours, preferably at least partially in an atmosphere comprising oxygen, wherein the heat-treating according to (d) is preferably partially carried out in an inert gas atmosphere.
14. The process of any of embodiments 1 to 13, wherein in (e), the aqueous solution comprises an organic acid, preferably selected from the group consisting of oxalic acid, acetic acid, citric acid, methane sulfonic acid, and a mixture of two or more thereof, and/or comprises an inorganic acid, preferably selected from the group consisting of phosphoric acid, sulphuric acid, hydrochloric acid, nitric acid, and a mixture of two or more thereof, the inorganic acid more preferably being nitric acid.

15. The process of any of embodiments 1 to 14, wherein in (e), the aqueous solution has a pH in the range of from 0 to 5, preferably from 0 to 3.5, more preferably from 0 to 2.

16. The process of any of embodiments 1 to 15, wherein in (d), the heat-treated material is treated with the aqueous solution at a temperature in the range of from 20 to 130° C., preferably from 50 to 120° C., more preferably from 90 to 110° C.

17. The process of any of embodiments 1 to 16, wherein in (d), the heat-treated zeolitic material is treated with the aqueous solution for a time period in the range of from 10 min to 40 h, preferably from 30 min to 30 h, more preferably from 1 h to 25 h.

18. The process of any of embodiments 1 to 17, wherein in (d), the heat-treated zeolitic material is treated with the aqueous solution at a weight ratio of the aqueous solution relative to the heat-treated zeolitic material in the range of from 2:1 to 50:1, preferably from 8:1 to 40:1, more preferably from 10:1 to 35:1.

19. The process of any of embodiments 1 to 18, further comprising
  (f) drying and/or calcining the zeolitic material obtained from (e), optionally from (e), optionally after washing, wherein the drying is preferably carried out at a temperature in the range of from 100 to 180° C., preferably from 120 to 150° C., for a period in the range of from 10 to 70 h, preferably from 15 to 25 h, and calcination is preferably carried out at a temperature in the range of from 550 to 700° C., preferably from 600 to 680° C., for a period in the range of from 1 to 10 h, preferably from 2 to 5 h.

20. The process of any of embodiments 1 to 19, further comprising
  (g) shaping the tin-containing zeolitic material having a BEA framework structure obtained from (d) or (e) or (f), preferably from (f), obtaining a molding;
  (h) drying and/or calcining the molding obtained from (g);
  (j) optionally subjecting the molding obtained from (g) or (h), preferably from (h), to a water-treatment, wherein the water-treatment comprises treating the molding with liquid water in an autoclave under autogenous pressure at a temperature in the range of from 100 to 200° C.;
  (k) optionally drying and/or calcining the water-treated molding obtained from (j).

21. The process of embodiment 20, wherein (j) comprises
  (j.1) preparing a mixture comprising the tin-containing zeolitic material having a BEA framework structure and an aqueous solution having a pH of at most 5;
  (j.2) adding a binder or a precursor thereof, preferably a silica binder or a precursor thereof, preferably a pore-forming agent, and optionally a plasticizing agent to the mixture obtained from (j.1);
  (j.3) subjecting the mixture obtained from (j.2) to shaping.

22. The process of embodiment 20 or 21, wherein (k) comprises
  (k.1) drying the molding obtained from (j) at a temperature in the range of from 75 to 200° C., preferably from 90 to 170° C., more preferably from 100 to 150° C.;
  (k.2) calcining the dried molding obtained from (k.1) at a temperature in the range of from 400 to 650° C., preferably from 450 to 600° C., more preferably from 475 to 550° C.

23. A tin-containing zeolitic material having a BEA framework structure, obtainable or obtained by a process according to any of embodiments 1 to 19 or 20 to 22.

24. A tin-containing zeolitic material having a BEA framework structure comprising $X_2O_3$ and $YO_2$, wherein Y is a tetravalent element selected from the group consisting of Si, Ti, Zr, Ge, and combinations of two or more thereof, Y preferably being Si, X is a trivalent element selected from the group consisting of B, In, Ga, Fe, and combinations of two or more thereof, X preferably being B, wherein the framework structure additionally comprises tin, wherein in the framework structure of the zeolitic material, the molar ratio $X_2O_3:YO_2$, preferably $B_2O_3:SiO_2$, is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-% of the framework structure of the zeolitic material consist of X, Y, O, H, and tin, preferably of B, Si, O, and tin, and wherein the tin-containing zeolitic material has a water adsorption of at most 12 weight-%, preferably at most 10 weight-%.

25. The tin-containing zeolitic material of embodiment 24, having a tin content in the range of from 0.1 to 20 weight-%, preferably from 0.5 to 18 weight-%, more preferably from 1 to 16 weight-%, more preferably from 2 to 14 weight-%, based on the total weight of the tin-containing zeolitic material.

26. The tin-containing zeolitic material of embodiment 24 or 25, having a UV/Vis spectrum exhibiting a maximum in the range of from 200 to 220 nm.

27. The tin-containing zeolitic material of any of embodiments 24 to 26, having an XRD spectrum exhibiting peaks at 2theta values at (21.5±0.2) °, (22.6±0.2)°, (25.5±0.2)°, (26.6±0.2)°, (28.8±0.2) °, (29.7±0.2) °, (32.2±0.2) °, (34.0±0.2) °, (37.9±0.2)°.

28. The tin-containing zeolitic material of any of embodiments 24 to 27, obtainable or obtained by a process according to any of claims 1 to 19.

29. The tin-containing zeolitic material of any of embodiments 24 to 28, comprised in a molding, said molding preferably additionally comprising a binder, preferably a silica binder.

Therefore, the present invention also relates to the process for preparing a compound of formula (III), comprising
(i) oxidizing a compound of formula (I) of which more than 50% are present as compound of formula (Ia)

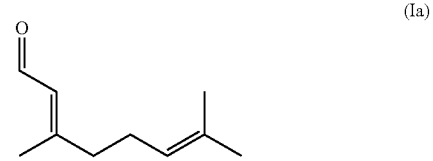

(Ia)

with hydrogen peroxide in the presence of a catalyst comprising a tin-containing zeolitic material of framework structure type BEA, said catalyst comprising a tin-containing zeolitic material of framework structure type BEA being obtainable or obtained by a process comprising incorporating the tin into a zeolitic material having a BEA framework structure and having vacant tetrahedral framework sites by a solid-state ion-exchange method, wherein the tin-containing zeolitic material of framework structure type BEA preferably has a tin content in the range of from 2 to 14 weight-% based on the total weight of the tin-containing molecular zeolitic material, wherein preferably at least 99 weight-% of the framework structure of the tin-containing zeolitic material of framework structure type BEA consist of Sn, O, H, Si, and B, and wherein in the framework structure of the tin-containing zeolitic material of framework structure type BEA, the molar ratio $B_2O_3:SiO_2$ is preferably in the range of from 0.001:1 to 0.01:1, obtaining a reaction mixture.

Thus, the present invention also relates to the process for preparing a compound of formula (III), wherein the tin-containing zeolitic material comprising, preferably consisting of, the structure type BEA, is obtainable or obtained by a process comprising (a) providing a zeolitic material having a BEA framework structure comprising $X_2O_3$ and $YO_2$, wherein Y is a tetravalent element selected from the group consisting of Si, Ti, Zr, Ge, and combinations of two or more thereof, preferably Si, and X is a trivalent element selected from the group consisting of B, In, Ga, Fe, and combinations of two or more thereof, preferably B, said BEA framework structure having vacant tetrahedral framework sites;

(b) providing a tin-ion source in solid form, preferably tin(II) acetate;

(c) incorporating tin into the zeolitic material provided in (a) by bringing the zeolitic material provided in (a) in contact with the tin-ion source provided in (b) under solid-state ion exchange conditions, preferably comprising mixing the zeolitic material provided in (a) with the tin-ion source and grinding and/or milling the mixture of the zeolitic material provided in (a) and the tin-ion source, obtaining a tin-containing zeolitic material having a BEA framework structure;

(d) subjecting the zeolitic material obtained from (c) to a heat treatment, preferably comprising calcining the zeolitic material obtained from (c), preferably at a temperature in the range of from 400 to 700° C.;

(e) optionally treating the heat-treated zeolitic material obtained from (d) with an aqueous solution having a pH of at most 5, more preferably a pH in the range of from 0 to 2;

said process optionally further comprising (f) drying and/or calcining the zeolitic material obtained from (e), optionally after washing, wherein the drying is preferably carried out at a temperature in the range of from 100 to 180° C. for a period in the range of from 10 to 70 h, and calcination is preferably carried out at a temperature in the range of from 550 to 700° C. for a period in the range of from 1 to 10 h;

wherein according to (a), the zeolitic material having a BEA framework structure having vacant tetrahedral framework sites is preferably provided by a method comprising (a.1) providing a zeolitic starting material having a BEA framework structure, wherein the framework structure of the zeolitic starting material comprises $X_2O_3$ and $YO_2$ and the molar ratio $X_2O_3:YO_2$ is greater than 0.02:1, preferably in the range of from 0.03:1 to 0.05:1;

(a.2) creating vacant tetrahedral framework sites by treating the zeolitic starting material provided in (a.1) with a liquid solvent system, preferably under reflux, obtaining a zeolitic material having a molar ratio $X_2O_3:YO_2$ of at most 0.02:1, wherein the liquid solvent system is preferably water, wherein more preferably, the liquid solvent system does not contain an inorganic or organic acid, or a salt thereof, and wherein the treating is preferably carried out at a temperature in the range of from 50 to 125° C., preferably for a period in the range of from 6 to 20 h;

(a.3) at least partially separating the zeolitic material obtained from (a.2) from the liquid solvent system, optionally including drying;

(a.4) optionally calcining the separated zeolitic material obtained from (a.3), preferably at a temperature in the range of from 400 to 700° C., and preferably for a time period in the range of from 1 to 10 h.

According to (i), the compound of formula (I) is oxidized with hydrogen peroxide. Generally, it may be conceivable that a suitable hydrogen peroxide source is employed. Thus, it may conceivable that in the reaction mixture according to (i), the hydrogen peroxide is suitably formed in situ. Preferably, the hydrogen peroxide is employed as an aqueous solution containing hydrogen peroxide. Preferably, the aqueous solution contains the hydrogen peroxide in an amount in the range of from 25 to 85 weight-%, more preferably in the range of from 25 to 80 weight-%, more preferably in the range of from 25 to 75 weight-%, based on the total weight of the aqueous solution. Depending on the solvent which is preferably contained in the reaction mixture, it was found that more than one liquid phase is present when the concentration of the hydrogen peroxide in the aqueous solution is comparatively low, such as in the range of from 25 to 55 weight-% or in the range of from 25 to 45 weight-% or in the range of from 25 to 35 weight-%. Since the presence of more than one liquid phase usually tends to complicate the process design, it is preferred that the aqueous solution contains the hydrogen peroxide in an amount in the range of from 65 to 75 weight-%, based on the total weight of the aqueous solution.

Preferably, at the beginning of the oxidizing in (i), the molar ratio of the compound of formula (I) relative to the hydrogen peroxide is at least 1:1, more preferably in the range of from 10:1 to 1:1, more preferably in the range of from 9:1 to 1:1, more preferably in the range of from 8:1 to 1:1, more preferably in the range of from 7:1 to 1:1, more preferably in the range of from 6:1 to 1:1, more preferably in the range of from 5:1 to 1:1, more preferably in the range of from 4:1 to 1:1, more preferably in the range of from 3:1 to 1:1. More preferably, at the beginning of the oxidizing in (i), the molar ratio of the compound of formula (I) relative to the hydrogen peroxide is in the range of from 2:1 to 1:1, more preferably in the range of from 1.5:1 to 1:1, more preferably in the range of from 1.3:1 to 1:1 such as in the range of from 1.3:1 to 1.2:1 or from 1.2:1 to 1.1:1 or from 1.1:1 to 1:1.

Preferably, the oxidizing in (i) is carried out in solvent. Regarding the chemical nature of the solvent, no specific restrictions exist, provided that the process of the present can be carried out. Preferably, the solvent comprises, more preferably is, an organic solvent. More preferably, the solvent comprises, more preferably is, one or more of alcohols, esters, ethers, optionally suitably substituted alkanes, nitriles.

It may be preferred that the solvent comprises, preferably consists of, one or more alcohols, preferably one or more C4 alcohols, one or more C5 alcohols, one or more C6 alcohols, one or more C7 alcohols, one or more C8 alcohols, one or more C9 alcohols, or a mixture of two or more thereof. Preferably, the one or more alcohols comprise, preferably consist of, one or more of tert-butanol, 2-methyl-2-butanol, n-pentanol, 3-methyl-1-butanol, n-hexanol, 2-methyl-1-pentanol, 3-heptanol, 2-ethyl-1-hexanol, 2-octanol, 1-octanol, 2,4,4-trimethyl-1-hexanol, 2,6-dimethyl-4-heptanol, 2-propyl-1-heptanol, and 2-propyl-5-methyl-1-hexanol. More preferably, the one or more alcohols comprise, preferably consist of, one or more of 2-ethyl-1-hexanol and 3-heptanol.

Therefore, the present invention also relates to the process for preparing a compound of formula (III), comprising
(i) oxidizing a compound of formula (I) of which more than 50% are present as compound of formula (Ia)

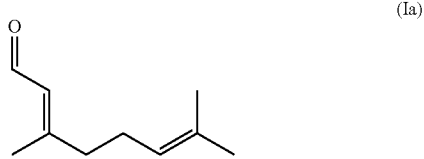

(Ia)

with hydrogen peroxide in the presence of a catalyst comprising a tin-containing zeolitic material of framework structure type BEA in a solvent comprising, preferably consisting of, one or more of 2-ethyl-1-hexanol and 3-heptanol, obtaining a reaction mixture.

Therefore, the present invention also relates to the process for preparing a compound of formula (III), comprising
(i) oxidizing a compound of formula (I) of which more than 50% are present as compound of formula (Ia)

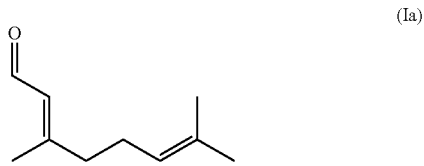

(Ia)

with hydrogen peroxide in the presence of a catalyst comprising a tin-containing zeolitic material of framework structure type BEA in a solvent comprising, preferably consisting of, one or more of 2-ethyl-1-hexanol and 3-heptanol, said catalyst comprising a tin-containing zeolitic material of framework structure type BEA being obtainable or obtained by a process comprising incorporating the tin into a zeolitic material having a BEA framework structure and having vacant tetrahedral framework sites by a solid-state ion-exchange method, wherein the tin-containing zeolitic material of framework structure type BEA preferably has a tin content in the range of from 2 to 14 weight-% based on the total weight of the tin-containing molecular zeolitic material, wherein preferably at least 99 weight-% of the framework structure of the tin-containing zeolitic material of framework structure type BEA consist of Sn, O, H, Si, and B, and wherein in the framework structure of the tin-containing zeolitic material of framework structure type BEA, the molar ratio $B_2O_3:SiO_2$ is preferably in the range of from 0.001:1 to 0.01:1, obtaining a reaction mixture.

With regard to the amount of solvent used in (i), no specific restrictions provided that the process of the invention can be carried out. Preferably, at the beginning of the oxidizing in (i), the weight ratio of the compound of formula (I) relative to the solvent is at most 1:2. More preferably, at the beginning of the oxidizing in (i), the weight ratio of the compound of formula (I) relative to the solvent is in the range of from 1:10 to 1:2, more preferably in the range of from 1:9 to 1:2, more preferably in the range of from 1:8 to 1:2, more preferably in the range of from 1:7 to 1:2, more preferably in the range of from 1:6 to 1:2, more preferably in the range of from 1:5 to 1:2, more preferably in the range of from 1:4 to 1:2, such as in the range of from 1:4 to 1:3.5 or from 1:3.5 to 1:3 or from 1:3 to 1:2.5 or from 1:2.5 to 1:2.

The temperature at which the oxidizing in (i) is carried out may depend on the solvent used in (i). Preferably, the solvent will be chosen so that the oxidizing in (i) can be carried out at temperature of the reaction mixture in the range of from 30 to 90° C., more preferably in the range of from 35 to 85° C., more preferably in the range of from 40 to 80° C., more preferably in the range of from 45 to 70° C., more preferably in the range of from 50 to 60° C. Therefore, the oxidizing in (i) is preferably carried out at temperature of the reaction mixture in the range of from 30 to 90° C., more preferably in the range of from 35 to 85° C., more preferably in the range of from 40 to 80° C., more preferably in the range of from 45 to 70° C., more preferably in the range of from 50 to 60° C., such as in the range of from 50 to 55° C. or from 55 to 60° C.

It may be preferred that in a first reaction step in (i), the compound of formula (I) and the catalyst, preferably together with the solvent, are heated to the above-mentioned temperature and, once this temperature of the mixture is reached, the hydrogen peroxide, preferably in the form of the aqueous solution, is added to the mixture at this temperature. The oxidizing in (i) can be carried out at more than two reaction temperatures.

According to a preferred embodiment of the present invention, the oxidizing in (i) is carried out in batch mode. Regarding this embodiment, the catalyst used in (i) is preferably employed as powder or as spray-powder or as spray-granulate. During spraying, it is possible that at least one binder and/or with at least one binder precursor is added which is then comprised in the spray-powder or spray-granulate. Suitable binders are described hereinunder in the context of the moldings which are preferably used in a continuous reaction. It is further preferred that according to this batch mode embodiment, at least 90 weight-%, more preferably at least 91 weight-%, more preferably at least 92 weight-%, more preferably at least 93 weight-%, more preferably at least 94 weight-%, more preferably at least 95 weight-%, more preferably at least 96 weight-%, more preferably at least 97 weight-%, more preferably at least 98 weight-%, more preferably at least 99 weight-% of the catalyst consist of the tin-containing molecular sieve. Yet further, it is preferred that according to this embodiment, the oxidizing in (i) is carried out for a period of time In the range of from 3 to 600 min, preferably in the range of from 30 to 500 min, more preferably in the range in the range of from 60 to 400 min. Further, it may be preferred that according to this embodiment, the oxidizing in (i) is carried out for a period of time in the range of from 1 to 25 min, preferably in the range of from 2 to 20 min, more preferably in the range of from 3 to 15 min.

According to a conceivable embodiment of the present invention, the oxidizing in (i) is carried out in continuous mode. According to this embodiment, it is preferred that a molding is employed prepared based on the tin-containing molecular sieve. In such a process for preparing said molding, the tin-containing molecular sieve, optionally after further modification, is suitably shaped and optionally post-treated. For the shaping, for example mentioned above in the embodiments in (g), the tin-containing molecular sieve can be admixed with at least one binder and/or with at least one binder precursor, and optionally with at least one pore-forming agent and/or at least one plasticizing agent. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum trilisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaoline, hectorite, bentonites, halloysites, dickites, nacrites or anaxites. These binders can be used as such or in the form of suitable precursor compounds which, either during spray-drying or spray-granulation and/or the calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, may be preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being In the range of from 50 to 500 $m^2/g$. Colloidal silica, preferably as an alkaline and/or ammoniacal solution, more preferably as an ammoniacal solution, is commercially available, inter alia, for example as Ludox®, Syton®, Nalco® or Snowtex®, Snowtexudoxca, preferably as an alkaline and/or ammr alia, for example as Hi-Sil®, Ultrasil®, Vulcasil®, Santocel®, Valron-Estersil®, Tokusil® or Nipsil®. r Nipsilstersille as Hi-Silas an alkaline able, inter alia, for example as Aerosil®, Reolosil®, Cab-O-Sil®, Fransil® or ArcSilica®. Inter alia, an ammoniacal solution of colloidal silica is preferred in the present invention. Pore forming agents include, but are not limited to, polymers such as polymeric vinyl compounds, such as polyalkylene oxides like polyethylene oxides, polystyrene, polyacrylates, polymethacrylates, polyolefins, polyamides and polyesters, carbohydrates, such as cellulose or cellulose derivatives like methyl cellulose, or sugars or natural fibers. Further suitable pore forming agents may be, for example, pulp or graphite. If desired with regard to the pore characteristics be achieved, a mixture of two or more pore forming agents may be used. In a particularly preferred embodiment, the pore forming agents are removed by calcination according to (h) and/or (k), as mentioned above. As to the ratio of the amount of the tin-containing molecular sieve relative to the amount of binder in the molding, it generally can be freely chosen. Generally, the weight ratio of the tin-containing molecular sieve relative to binder is in the range of from 20:1 to 1:20, preferably from 10:1 to 1:10, more preferably from 1:1 to 1:10. For preparing a molding based on the tin-containing molecular sieve, at last one pasting agent can be used to provide for an improved processability of the moldable mixture. Conceivable pasting agents are, among others, organic, in particular hydrophilic polymers, such as, for example, carbohydrates like cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, carbohydrates such as cellulose, cellulose derivatives, water and mixtures of two or more of these compounds, such as water and cellulose or water and cellulose derivatives are used as pasting agent. In a particularly preferred embodiment of the process according to the invention, the at least one pasting agent is removed by drying and/or calcination.

Generally, the process conditions are preferably chosen so that the oxidizing in (i) is carried out so that during oxidizing, the hydrogen peroxide conversion is at least in the range of from 60 to 80%, such as at least 60% or at least 70% or at least 80%. In particular, during the oxidizing in (i), the temperature of the reaction mixture and the reaction time are preferably chosen so that during oxidizing, the hydrogen peroxide conversion is at least in the range of from 60 to 80%.

From the oxidizing In (i), a reaction mixture is obtained which comprises, as main product of the Baeyer-Villiger oxidation, the compound of formula (II)

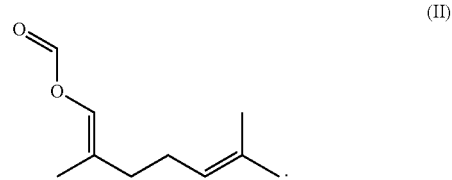

Additionally, the reaction mixture obtained from (i), may also comprise the compound of formula (III). Since the compound of formula of formula (III)

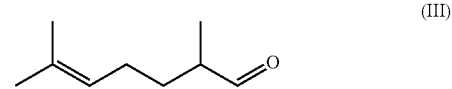

can be formed from the enol formate of formula (II) by straightforward hydrolysis, the selectivity values to melonal described in the context of the present invention refer to the selectivity values to the sum of the compound of formula (II) and the compound of formula (III) contained in the reaction mixture obtained from (i).

Since melonal is the major product, it is preferred that after (i), the compound of formula (II) is suitably hydrolyzed, obtaining a mixture containing the compound of formula (III). Therefore, the present invention also relates process for preparing a compound of formula (III)

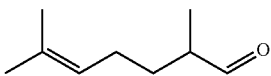

said process comprising
(i) oxidizing a compound of formula (I)

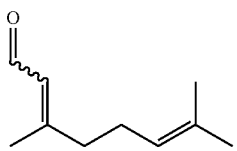

of which more than 50% are present as compound of formula (Ia)

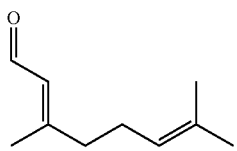

with hydrogen peroxide in the presence of a catalyst comprising a tin-containing molecular sieve, obtaining a reaction mixture comprising a compound of formula (II)

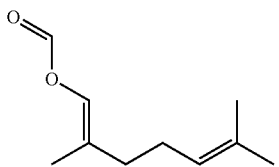

and optionally the compound of formula (III),
wherein after (i), the mixture comprising the compound of formula (II) and optionally the compound of formula (III) is subjected to hydrolyzing conditions, thus hydrolyzing the compound of formula (II), obtaining a mixture containing the compound of formula (III). Preferably, prior to subjecting the mixture comprising the compound of formula (II) and optionally the compound of formula (III) to hydrolyzing conditions, the catalyst comprising a tin-containing molecular sieve is suitably separated from said mixture. Preferably, prior to subjecting the mixture comprising the compound of formula (II) and optionally the compound of formula (III) to hydrolyzing conditions, more preferably prior to suitably separating the catalyst comprising a tin-containing molecular sieve from said mixture, the reaction mixture obtained from (i) is cooled, preferably to a temperature In the range of from 5 to 40° C., more preferably in the range of from 8 to 20° C., more preferably In the range of from 10 to 15° C. Preferably, after hydrolyzing the compound of formula (II), the compound of formula (III) is suitably separated from the mixture obtained from said hydrolyzing.

Therefore, the present invention also relates to the process as defined above, further comprising (ii) preferably separating the Baeyer-Villiger catalyst, preferably a catalyst comprising a tin-containing molecular sieve, from the mixture obtained from (i);
(iii) hydrolyzing the compound of formula (II), obtaining a mixture containing the compound of formula (III);
(iv) preferably separating the compound of formula (III) from the mixture obtained from (iii).

Thus, the present invention also relates to the process as defined above, further comprising (ii) separating the Baeyer-Villiger catalyst, preferably a catalyst comprising a tin-containing molecular sieve, from the mixture obtained from (i);
(iii) hydrolyzing the compound of formula (II), obtaining a mixture containing the compound of formula (III);
(iv) separating the compound of formula (III) from the mixture obtained from (iii).

Regarding the separating according to (ii), no specific restrictions exist. If, for example, the process of the invention is carried out in batch mode, it is preferred that the separating comprises, preferably consists of, subjecting the mixture obtained from (i) to filtration. Other separation methods such as phase separation methods are also an option. Generally, it is conceivable that the catalyst contained in the respectively obtained filter cake is re-used, after having been optionally suitably regenerated, as catalyst in (i).

The hydrolyzing in (ill) can be carried out by any method which leads to the compound of formula (III). Preferably, for hydrolyzing in (iii), an aqueous base is added to the mixture obtained from (i), preferably from (ii). Preferably, the aqueous base is an aqueous solution of an inorganic base, more preferably an aqueous solution of a hydroxide, more preferably an aqueous solution of an alkali metal hydroxide, more preferably an aqueous solution of sodium hydroxide. Preferably, the aqueous sodium hydroxide solution contains the sodium hydroxide in an amount in the range of from 1 to 25 weight-%, preferably in the range of from 2 to 20 weight-%, more preferably in the range of from 5 to 15 weight-%, based on the total weight of the aqueous sodium hydroxide solution. Preferably, the aqueous base is added to the reaction mixture at a temperature of the reaction mixture in the range of from 5 to 40° C., preferably in the range of from 8 to 20° C., more preferably in the range of from 10 to 15° C.

By adding the aqueous base to the reaction mixture obtained from the oxidizing in (i) and preferably the separating in (ii), an organic phase containing the compound of formula (III) and an aqueous phase are obtained. Therefore, it is preferred that the separating of the compound of formula (III) from the mixture obtained from (iii) comprises separating the organic phase from the aqueous phase, wherein the organic phase comprising the compound of formula (III) is preferably suitably washed, preferably with a washing agent comprising water. More preferably, at least 95 weight-%, preferably at least 99 weight-%, more preferably at least 99.9 weight-% of the washing agent consist of water. Said washing is can be carried out at any suitably temperature, wherein the temperature of the washing agent is preferably in the range of from 5 to 40° C., more preferably in the range of from 10 to 30° C., more preferably in the range of from 15 to 25° C.

While it is generally conceivable that the organic phase separated from the aqueous phase and preferably washed is used as such, it is preferred that the compound of formula (III) is suitably separated from the organic phase. Regarding this separating, no specific restrictions exist, provided that the compound of formula (III) is obtained in separated form.

Preferably, said separating of the compound of formula (III) from the organic phase comprises distillation, preferably fractional distillation.

Mixtures

Generally, the present invention also relates to a mixture, obtainable or obtained by a process according to the present invention, preferably the reaction mixture as obtainable or obtained from step (i) of the process of the present invention.

According to the present invention, it was found that the use of the compound of formula (I) wherein more than 50% of the compound of formula (I) are present as compound of formula (Ia) exhibits an advantage over the teaching of the prior art exclusively relating to the use of a 1:1 mixture of the compound of formula (Ia) and of formula (Ib). The starting material of the novel and inventive process is the mixture which is employed as starting mixture for the Baeyer-Villiger oxidation in (i).

Therefore, the present invention also relates to this mixture, in particular to a mixture comprising a compound of formula (I)

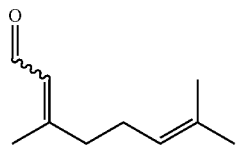

(I)

wherein more than 50%, preferably at least 55%, more preferably at least 60%, more preferably at least 65%, more preferably at least 70%, more preferably at least 75%, more preferably at least 80%, more preferably at least 85%, more preferably at least 90%, more preferably at least 95%, more preferably at least 96%, more preferably at least 97%, more preferably at least 98% of the compound of formula (I) are present as compound of formula (Ia)

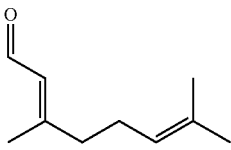

(Ia)

and a Baeyer-Villiger oxidation catalyst which preferably comprises a tin-containing molecular sieve, preferably a tin-containing molecular sieve as defined hereinabove, more preferably a tin-containing zeolitic material as defined hereinabove, more preferably a tin-containing zeolitic material having framework structure type BEA as defined hereinabove, more preferably a tin-containing zeolitic material having framework structure type BEA obtainable or obtained by a method comprising incorporating tin in a zeolitic material having framework structure type BEA via a solid-state ion-exchange method as defined hereinabove. Preferably, this mixture further comprising a solvent, more preferably a solvent as described hereinabove. In said mixture, the weight ratio of the compound of formula (I) relative to the solvent is preferably in the range of from 1:10 to 1:2, preferably in the range of from 1:5 to 1:2, more preferably in the range of from 1:4 to 1:2.

Uses

As mentioned above, it was found that the use of the compound of formula (I) wherein more than 50% of the compound of formula (I) are present as compound of formula (Ia) exhibits an advantage over the teaching of the prior art exclusively relating to the use of a 1:1 mixture of the compound of formula (Ia) and of formula (Ib).

Therefore, the present invention also relates to the use of a compound of formula (I)

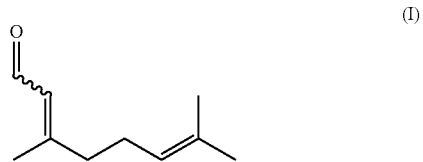

(I)

of which more than 50%, preferably at least 55%, more preferably at least 60%, more preferably at least 65%, more preferably at least 70%, more preferably at least 75%, more preferably at least 80%, more preferably at least 85%, more preferably at least 90%, more preferably at least 95%, more preferably at least 96%, more preferably at least 97%, more preferably at least 98% are present as compound of formula (Ia)

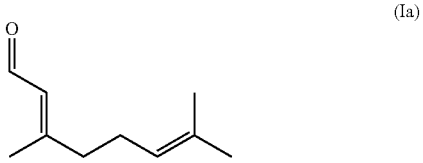

(Ia)

for either increasing the selectivity and/or decreasing the reaction time of the Baeyer-Villiger oxidation of the compound of formula (I) for preparing a compound of formula (III)

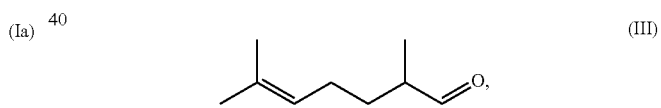

(III)

compared to the respective Baeyer-Villiger oxidation of the compound of formula (I) of which at most 50% are present as compound of formula (Ia), at otherwise identical oxidation conditions.

Further, the present invention also relates to the use of the starting mixture described above, in particular a mixture comprising a compound of formula (I)

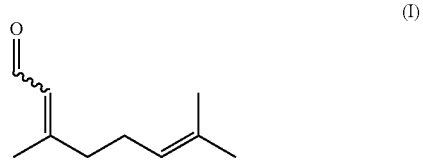

(I)

wherein more than 50%, preferably at least 55%, more preferably at least 60%, more preferably at least 65%, more preferably at least 70%, more preferably at least 75%, more preferably at least 80%, more preferably at least 85%, more preferably at least 90%, more preferably at least 95%, more preferably at least 96%, more preferably at least 97%, more preferably at least 98% of the compound of formula (I) are present as compound of formula (Ia)

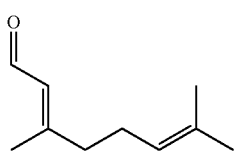
(Ia)

and a Baeyer-Villiger oxidation catalyst which preferably comprises a tin-containing molecular sieve, preferably a tin-containing molecular sieve as defined hereinabove, more preferably a tin-containing zeolitic material as defined hereinabove, more preferably a tin-containing zeolitic material having framework structure type BEA as defined hereinabove, more preferably a tin-containing zeolitic material having framework structure type BEA obtainable or obtained by a method comprising incorporating tin in a zeolitic material having framework structure type BEA via a solid-state ion-exchange method as defined hereinabove. Preferably, this mixture further comprising a solvent, more preferably a solvent as described hereinabove. In said mixture, the weight ratio of the compound of formula (I) relative to the solvent is preferably in the range of from 1:10 to 1:2, preferably in the range of from 1:5 to 1:2, more preferably in the range of from 1:4 to 1:2, for either increasing the selectivity and/or decreasing the reaction time of the Baeyer-Villiger oxidation of the pound of formula (III)

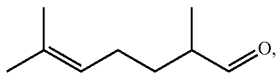
(III)

compared to the respective Baeyer-Villiger oxidation of the compound of formula (I) of which at most 50% are present as compound of formula (Ia), at otherwise identical oxidation conditions.

Still further, the present invention also relates to the use of said starting mixture for preparing a compound of formula (II)

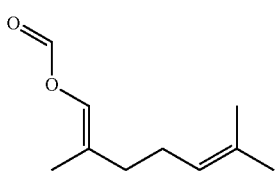
(II)

and/or for preparing a compound of formula (III)

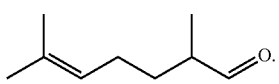
(III)

The present invention is further illustrated by the following embodiments and combinations of embodiments according to the dependencies and references as indicated:

1. A process, preferably a liquid-phase process, for preparing a compound of formula (III)

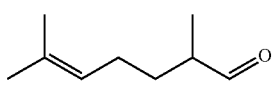
(III)

said process comprising
(i) oxidizing a compound of formula (I)

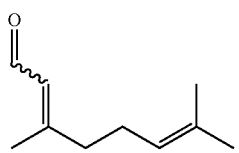
(I)

of which more than 50% are present as compound of formula (Ia)

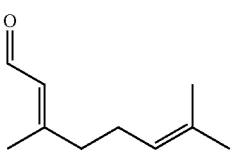
(Ia)

with hydrogen peroxide in the presence of a Baeyer-Villiger catalyst, preferably a catalyst comprising a tin-containing molecular sieve, obtaining a reaction mixture comprising a compound of formula (II

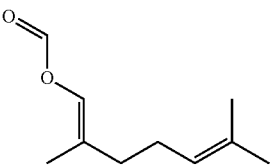
(II)

and optionally the compound of formula (III).

2. The process of embodiment 1, wherein in (i), at least 55%, preferably at least 65%, more preferably at least 75%, more preferably at least 80%, more preferably at least 90% of the compound of formula (I) are present as compound of formula (Ia).

3. The process of embodiment 1 or 2, wherein in (i), at least 95%, preferably at least 96%, more preferably at least 97%, more preferably at least 98% of the compound of formula (I) are present as compound of formula (Ia).

4. The process of any one of embodiments 1 to 3, wherein in (i), the tin-containing molecular sieve comprises micropores, or mesopores, or micropores and mesopores.

5. The process of any one of embodiments 1 to 4, wherein in (I), the tin-containing molecular sieve comprises, preferably consists of, a mesoporous molecular sieve.

6. The process of embodiment 5, wherein the tin-containing molecular sieve comprises, preferably consists of, MCM-41.

7. The process of any one of embodiments 1 to 4, wherein in (i), the tin-containing molecular sieve comprises, preferably consists of, a tin-containing microporous molecular sieve.

8. The process of embodiments 7, wherein the tin-containing microporous molecular sieve is a tin-containing zeolitic material.

9. The process of embodiment 8, wherein in (i), the framework structure type of the tin-containing zeolitic material is selected from the group consisting of ABW, ACO, AEI, AEL, AEN, AET, AFG, AFI, AFN, AFO, AFR, AFS, AFT, AFV, AFX, AFY, AHT, ANA, APC, APD, AST, ASV, ATN, ATO, ATS, ATT, ATV, AVL, AWO, AWW, BCT, BEA, BEC, BIK, BOF, BOG, BOZ, BPH, BRE, BSV, CAN, CAS, CDO, CFI, CGF, CGS, CHA, CHI, CLO, CON, CZP, DAC, DDR, DFO, DFT, DOH, DON, EAB, EDI, EEI, EMT, EON, EPI, ERI, ESV, ETR, EUO, EZT, FAR, FAU, FER, FRA, GIS, GIU, GME, GON, GOO, HEU, IFO, IFR, IFW, IFY, IHW, IMF, IRN, IRR, ITY, ISV, ITE, ITG, ITH, ITN, ITR, ITT, ITV, ITW, IWR, IWS, IWV, IWW, JBW, JOZ, JRY, JSN, JSR, JST, JSW, KFI, LAU, LEV, LIO, LIT, LOS, LOV, LTA, LTF, LTJ, LTL, LTN, MAR, MAZ, MEI, MEL, MEP, MER, MFI, MFS, MON, MOR, MOZ, MRE, MSE, MSO, MTF, MTN, MTT, MTW, MVY, MWW, NAB, NAT, NES, NON, NPO, NPT, NSI, OBW, OFF, OKO, OSI, OSO, OWE, PAR, PAU, PCR, PHI, PON, PUN, RHO, RON, RRO, RSN, RTE, RTH, RUT, RWR, RWY, SAF, SAO, SAS, SAT, SAV, SBE, SBN, SBS, SBT, SEW, SFE, SFF, SFG, SFH, SFN, SFO, SFS, SFV, SFW, SGT, SIV, SOD, SOF, SOS, SSF, SSO, SSY, STF, STI, STT, STW, SVR, SW, SZR, TER, THO, TON, TSC, TUN, UEI, UFI, UOS, UOV, UOZ, USI, UTL, UWY, VET, VFI, VNI, VSV, WEI, WEN, YUG, ZON, mixtures of two or more thereof, and mixed types of two or more thereof.

10. The process of any one of embodiments 7 to 9, wherein in (i), the framework structure type of the tin-containing zeolitic material is selected from the group consisting of BEA, MWW, MFI, mixtures of two or more thereof, and mixed types of two or more thereof.

11. The process of any one of embodiments 7 to 10, wherein in (i), the framework structure type of the tin-containing zeolitic material comprises, preferably consists of, the structure type BEA.

12. The process of any one of embodiments 1 to 11, wherein at least 95 weight-%, preferably at least 97 weight-%, more preferably at least 98 weight-% of the framework structure of the tin-containing molecular sieve consist of Sn, O, H, a tetravalent element Y, and optionally a trivalent element X.

13. The process of any one of embodiments 1 to 12, wherein at least 99 weight-%, preferably at least 99.5 weight-%, more preferably at least 99.9 weight-% of the framework structure of the tin-containing molecular sieve consist of Sn, O, H, a tetravalent element Y, and optionally a trivalent element X.

14. The process of embodiment 13, wherein Y comprises, preferably is, one or more of Si, Ge, Ti, and Zr, wherein Y more preferably comprises, more preferably is, Si.

15. The process of embodiment 13 or 14, wherein X comprises, preferably is, one or more of B, In, Ga, and Fe, wherein Y more preferably comprises, more preferably is, B.

16. The process of any one of embodiments 13 to 15, wherein X is not Al.

17. The process of any one of embodiments 1 to 16, wherein the tin-containing molecular sieve has a tin content in the range of from 0.1 to 20 weight-%, preferably from 0.5 to 18 weight-%, more preferably from 2 to 14 weight-%, based on the total weight of the tin-containing molecular sieve.

18. The process of any one of embodiments 1 to 16, wherein the tin-containing molecular sieve has a tin content in the range of from 8 to 14 weight-%, preferably from 10 to 14 weight-%, based on the total weight of the tin-containing molecular sieve.

19. The process of embodiment 18, wherein the tin-containing molecular sieve comprises, preferably consists of, a tin-containing zeolitic material and the framework structure type of the tin-containing zeolitic material comprises, preferably consists of, the structure type BEA.

20. The process of embodiment 19, wherein at least 99 weight-%, preferably at least 99.5 weight-%, more preferably at least 99.9 weight-% of the framework structure of the tin-containing zeolitic material consist of Sn, O, H, Si, and optionally B.

21. The process of embodiment 20, wherein in the framework structure of the tin-zeolitic material, the molar ratio $B_2O_3:SiO_2$ is at most 0.01:1, preferably in the range of from 0.001:1 to 0.01:1, more preferably in the range of from 0.001:1 to 0.003:1.

22. The process of any one of embodiments 19 to 21, wherein the tin-containing zeolitic material comprising, preferably consisting of, the structure type BEA, is obtainable or obtained by a process comprising
   (a) providing a zeolitic material having a BEA framework structure comprising $X_2O_3$ and $YO_2$, wherein Y is a tetravalent element selected from the group consisting of Si, Ti, Zr, Ge, and combinations of two or more thereof, preferably Si, and X is a trivalent element selected from the group consisting of B, In, Ga, Fe, and combinations of two or more thereof, preferably B, said BEA framework structure having vacant tetrahedral framework sites;
   (b) providing a tin-ion source in solid form, preferably tin(II) acetate;
   (c) incorporating tin into the zeolitic material provided in (a) by bringing the zeolitic material provided in (a) in contact with the tin-ion source provided in (b) under solid-state ion exchange conditions, preferably comprising mixing the zeolitic material provided in (a) with the tin-ion source and grinding and/or milling the mixture of the zeolitic material provided in (a) and the tin-ion source, obtaining a tin-containing zeolitic material having a BEA framework structure;
   (d) subjecting the zeolitic material obtained from (c) to a heat treatment, preferably comprising calcining the zeolitic material obtained from (c), preferably at a temperature in the range of from 400 to 700° C.;
   (e) optionally treating the heat-treated zeolitic material obtained from (d) with an aqueous solution having a pH of at most 5, more preferably a pH in the range of from 0 to 2;
   said process optionally further comprising
   (f) drying and/or calcining the zeolitic material obtained from (e), optionally after washing, wherein the drying is preferably carried out at a temperature in the range of from 100 to 180° C. for a period in the range of from 10 to 70 h, and calcination is preferably carried out at a temperature in the range of from 550 to 700 in the range of from 100 to 180° C. for a peri;

wherein according to (a), the zeolitic material having a BEA framework structure having vacant tetrahedral framework sites is preferably provided by a method comprising (a.1) providing a zeolitic starting material having a BEA framework structure, wherein the framework structure of the zeolitic starting material comprises $X_2O_3$ and $YO_2$ and the molar ratio $X_2O_3{:}YO_2$ is greater than 0.02:1, preferably in the range of from 0.03:1 to 0.05:1;

(a.2) creating vacant tetrahedral framework sites by treating the zeolitic starting material provided in (a.1) with a liquid solvent system, preferably under reflux, obtaining a zeolitic material having a molar ratio $X_2O_3{:}YO_2$ of at most 0.02:1, wherein the liquid solvent system is preferably water, wherein more preferably, the liquid solvent system does not contain an inorganic or organic acid, or a salt thereof, and wherein the treating is preferably carried out at a temperature in the range of from 50 to 125° C., preferably for a period in the range of from 6 to 20 h;

(a.3) at least partially separating the zeolitic material obtained from (a.2) from the liquid solvent system, optionally including drying;

(a.4) optionally calcining the separated zeolitic material obtained from (a.3), preferably at a temperature in the range of from 400 to 700° C., and preferably for a time period in the range of from 1 to 10 h.

23. The process of any one of embodiments 1 to 22, wherein in (i), the hydrogen peroxide is employed as an aqueous solution containing hydrogen peroxide, wherein the aqueous solution contains the hydrogen peroxide preferably in an amount in the range of from 25 to 85 weight-%, more preferably in the range of from 25 to 80 weight-%, more preferably in the range of from 25 to 75 weight-%, based on the total weight of the aqueous solution.

24. The process of embodiment 23, wherein the aqueous solution contains the hydrogen peroxide in an amount in the range of from 65 to 75 weight-%, based on the total weight of the aqueous solution.

25. The process of any one of embodiment 1 to 24, wherein at the beginning of the oxidation in (i), the molar ratio of the compound of formula (I) relative to the hydrogen peroxide is in the range of from 10:1 to 1:1, preferably in the range of from 5:1 to 1:1, more preferably in the range of from 3:1 to 1:1.

26. The process of any one of embodiment 1 to 25, wherein at the beginning of the oxidizing in (i), the molar ratio of the compound of formula (I) relative to the hydrogen peroxide is in the range of from 2:1 to 1:1, preferably in the range of from 1.5:1 to 1:1, more preferably in the range of from 1.3:1 to 1:1.

27. The process of any one of embodiments 1 to 26, wherein the oxidizing in (i) is carried out in a solvent, preferably in an organic solvent, preferably comprising one or more of alcohols, esters, ethers, optionally suitably substituted alkanes, nitriles.

28. The process of embodiment 27, wherein the solvent comprises, preferably consists of, one or more alcohols, preferably one or more C4 alcohols, one or more C5 alcohols, one or more C6 alcohols, one or more C7 alcohols, one or more C8 alcohols, one or more C9 alcohols, or a mixture of two or more thereof.

29. The process of embodiment 27 or 28, wherein the one or more alcohols comprise, preferably consist of, one or more of tert-butanol, 2-methyl-2-butanol, n-pentanol, 3-methyl-1-butanol, n-hexanol, 2-methyl-1-pentanol, 3-heptanol, 2-ethyl-1-hexanol, 2-octanol, 1-octanol, 2,4,4-trimethyl-1-hexanol, 2,6-dimethyl-4-heptanol, 2-propyl-1-heptanol, and 2-propyl-5-methyl-1-hexanol.

30. The process of any one of embodiment 27 to 29, wherein the one or more alcohols comprise, preferably consist of, one or more of 2-ethyl-1-hexanol and 3-heptanol.

31. The process of any one of embodiments 27 to 30, wherein the one or more alcohols comprise, preferably consist of, 2-ethyl-1-hexanol.

32. The process of any one of embodiments 27 to 31, wherein the one or more alcohols comprise, preferably consist of, 3-heptanol.

33. The process of any one of embodiments 27 to 32, wherein at the beginning of the oxidizing in (i), the weight ratio of the compound of formula (I) relative to the solvent is in the range of from 1:10 to 1:2, preferably in the range of from 1:5 to 1:2.

34. The process of any one of embodiments 27 to 33, wherein at the beginning of the oxidizing in (i), the weight ratio of the compound of formula (I) relative to the solvent is in the range of from 1:4 to 1:2.

35. The process of any one of embodiments 1 to 34, wherein the oxidizing in (i) is carried out at temperature of the reaction mixture in the range of from 30 to 90° C., preferably in the range of from 40 to 80° C., more preferably in the range of from 50 to 60° C.

36. The process of any one of embodiments 1 to 35, wherein the oxidizing in (i) is carried out in batch mode.

37. The process of any one of embodiments 1 to 36, preferably of embodiment 36, wherein the catalyst is employed as powder or spray-powder.

38. The process of embodiment 37, wherein at least 90 weight-%, preferably at least 95 weight-%, more preferably at least 99 weight-% of the catalyst consist of the tin-containing molecular sieve.

39. The process of any one of embodiments 1 to 38, preferably of any one of embodiments 36 to 38, wherein the oxidizing in (i) is carried out for a period of time in the range of from 3 to 600 min, preferably in the range of from 30 to 500 min, more preferably in the range in the range of from 60 to 400 min.

40. The process of any one of embodiments 1 to 39, preferably of any one of embodiments 36 to 39, wherein the oxidizing in (I) is carried out for a period of time in the range of from 1 to 25 min, preferably in the range of from 2 to 20 min, more preferably in the range of from 3 to 15 min.

41. The process of any one of embodiments 1 to 35, wherein the oxidizing in (i) is carded out in continuous-mode.

42. The process of embodiment 41, wherein the catalyst is employed as a molding containing the tin-containing molecular sieve and preferably a binder.

43. The process of embodiment 42, wherein the binder comprises, preferably is, a silica binder.

44. The process of embodiment 42 or 43, wherein the tin-containing molecular sieve is contained in the molding as powder or spray-powder.

45. The process of any one of embodiments 1 to 44, wherein the oxidizing in (i) is carried out so that during oxidizing, the hydrogen peroxide conversion is at least in the range of from 60 to 80%.

46. The process of any one of embodiments 1 to 45, wherein during the oxidizing in (i), the temperature of the reaction mixture and the reaction time are chosen so that during oxidizing, the hydrogen peroxide conversion is at least in the range of from 60 to 80%.

47. The process of any one of embodiments 1 to 46, preferably of any one of embodiments 1 to 44, further comprising
    (ii) preferably separating the Baeyer-Villiger catalyst, preferably a catalyst comprising a tin-containing molecular sieve, from the mixture obtained from (I);
    (iii) hydrolyzing the compound of formula (II), obtaining a mixture containing the compound of formula (III);
    (iv) preferably separating the compound of formula (III) from the mixture obtained from (iii).
48. The process of embodiment 47, wherein in (ii), the separating comprises, preferably consists of, subjecting the mixture obtained from (i) to filtration.
49. The process of embodiment 48, wherein in (iii), the hydrolyzing is carried out by adding an aqueous base to the reaction mixture obtained from the oxidizing in (i) and preferably the separating in (ii), obtaining an organic phase containing the compound of formula (III) and an aqueous phase.
50. The process of embodiment 49, wherein the aqueous base comprises, preferably is, an aqueous sodium hydroxide solution.
51. The process of embodiment 50, wherein the aqueous sodium hydroxide solution contains the sodium hydroxide in an amount in the range of from 1 to 25 weight-%, preferably in the range of from 2 to 20 weight-%, more preferably In the range of from 5 to 15 weight-%, based on the total weight of the aqueous sodium hydroxide solution.
52. The process of any one of embodiments 48 to 51, wherein in (iii), the aqueous base is added to the reaction mixture at a temperature of the reaction mixture in the range of from 5 to 40° C., preferably in the range of from 8 to 20° C., more preferably in the range of from 10 to 15° C.
53. The process of any one of embodiments 48 to 52, wherein in (iv), the separating of the compound of formula (III) from the mixture obtained from (iii) comprises separating the organic phase from the aqueous phase.
54. The process of any one of embodiments 48 to 53, preferably of embodiment 53, wherein the organic phase is washed, preferably with a washing agent comprising water.
55. The process of embodiment 54, wherein at least 95 weight-%, preferably at least 99 weight-%, more preferably at least 99.9 weight-% of the washing agent consist of water.
56. The process of embodiment 54 or 55, wherein the washing is carried out at a temperature of the washing agent in the range of from 5 to 40° C., preferably in the range of from 10 to 30° C., more preferably in the range of from 15 to 25° C.
57. The process of any one of embodiments 48 to 56, preferably of any one of embodiments 53 to 56, more preferably of any one of embodiments 54 to 56, wherein the compound of formula (III) is separated from the organic phase, preferably from the organic phase separated from the aqueous phase, more preferably from the washed organic phase.
58. The process of embodiment 57, wherein the separating of the compound of formula (III) from the organic phase comprises distillation, preferably fractional distillation.
59. A mixture, obtainable or obtained by a process according to any one of embodiments 1 to 46.
60. A mixture, obtainable or obtained by a process according to any one of embodiments 48 to 58.

61. A mixture comprising a compound of formula (I)

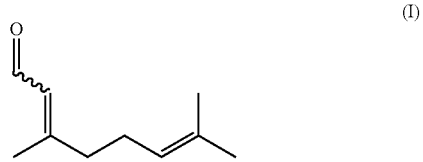

wherein more than 50% of the compound of formula (I) are present as compound of formula (Ia)

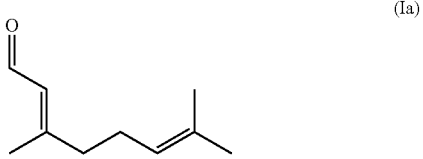

and a Baeyer-Villiger oxidation catalyst.

62. The mixture of embodiment 61, wherein the catalyst comprises a tin-containing molecular sieve, preferably a tin-containing molecular sieve as defined in any one of embodiments 4 to 21.
63. The mixture of embodiment 61 or 62, further comprising a solvent.
64. The mixture of embodiment 63, wherein the solvent comprises, preferably consists of, one or more alcohols, preferably as defined in any one of embodiments 28 to 32.
65. The mixture of embodiment 63 or 64, wherein in the mixture, the weight ratio of the compound of formula (I) relative to the solvent is in the range of from 1:10 to 1:2, preferably in the range of from 1:5 to 1:2, more preferably in the range of from 1:4 to 1:2.
66. Use of a compound of formula (I)

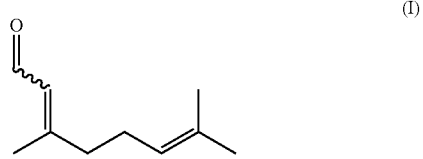

of which more than 50% are present as compound of formula (Ia)

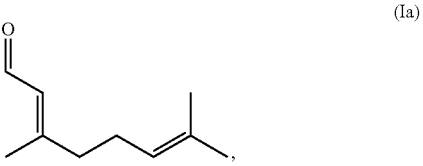

or use of a mixture according to any one of embodiments 61 to 65, for increasing the selectivity of the Baeyer-Villiger oxidation of the compound of formula (I) for preparing a compound of formula (III)

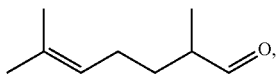
(III)

compared to the respective Baeyer-Villiger oxidation of the compound of formula (I) of which at most 50% are present as compound of formula (Ia), at otherwise identical oxidation conditions.
67. Use of a compound of formula (I)

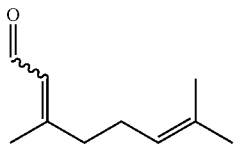
(I)

of which more than 50% are present as compound of formula (Ia)

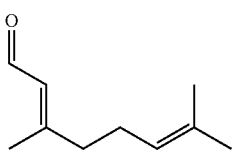
(Ia)

or use of a mixture according to any one of embodiments 61 to 65, for decreasing the reaction time of the Baeyer-Villiger oxidation of the compound of formula (I) for preparing a compound formula (III)

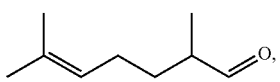
(III)

compared to the respective Baeyer-Villiger oxidation of the compound of formula (I) of which at most 50% are present as compound of formula (Ia), at otherwise identical oxidation conditions.
68. The use of embodiment 66 or 67, wherein the Baeyer-Villiger oxidation is carried using a catalyst comprising a tin-containing molecular sieve, preferably a tin-containing molecular sieve as defined in any one of embodiments 4 to 21.
69. The use of any one of embodiments 66 to 68, wherein the Baeyer-Villiger oxidation is carried out using hydrogen peroxide.
70. Use of a mixture according to any one of embodiments 61 to 65 for preparing a compound of formula (II)

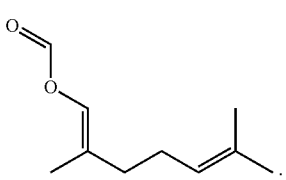
(II)

71. Use of a mixture according to any one of embodiments 61 to 65 for preparing a compound of formula (III)

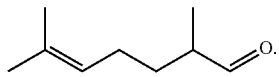
(III)

The present invention is further illustrated by the following reference examples and examples.

EXAMPLES

Reference Example 1: Determination of the Water Uptake

Water adsorption/desorption isotherms were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept isothermal during the measurement. The microbalance was calibrated, and the weight of the dried sample was balanced (maximum mass deviation 0.01 weight-%). Water uptake by the sample was measured as the increase in weight over that of the dry sample. First, as adsorption curve was measured by increasing the relative humidity (RH) (expressed as weight-% water in the atmosphere inside of the cell) to which the sample was exposed and measuring the water uptake by the sample as equilibrium. The RH was increased with a step of 10 weight-% from 5% to 85% and at each step the system controlled the RH and monitored the sample weight until reaching the equilibrium conditions after the sample was exposed from 85 weight-% to 5 weight-% with a step of 10% and the change in the weight of the sample (water uptake) was monitored and recorded.

Reference Example 2: Determination of the Crystallinity

The crystallinity of the zeolitic materials according to the present invention was determined by XRD analysis using the EVA method as described in the User Manual DIFFRAC.EVA Version 3, page 105, from Bruker AXS GmbH, Karlsruhe. The respective data were collected on a standard Bruker D8 Advance Diffractometer Series II using a Sol-X detector, from 2° to 50° 2theta, using variable slits (V20), a step size of 0.02° 2theta and a scan speed of 2.4 s/step. Default parameters were used for estimating the background/amorphous content (Curvature=1, Threshold=1).

Reference Example 3: FT-IR Measurements

The FT-IR (Fourier-Transformed-Infrared) measurements were performed on a Nicolet 6700 spectrometer. The powdered material was pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 cm$^{-1}$ at a resolution of 2 cm$^{-1}$. The obtained spectra are represented in a plot having on the x axis the wavenumber (cm$^{-1}$) and on the y axis the absorbance (arbitrary units, a.u.). For the quantitative determination of the peak heights and the ratio between these peaks a baseline correction was carried out. Changes in the 3000-3900 cm$^{-1}$ region were analyzed and for comparing multiple samples, as reference the band at 1880±5 cm-$^{1}$ was taken.

Reference Example 4: Determination of the Crush Strength of Moldings

The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1 S", version 1.5, December 2001 by Zwick GmbH & Co. Technische Dokumentation, August-Nagel-Strasse 11, D-89079 Ulm, Germany. With said machine, a given strand as described in Example 5, having a diameter of 1.5 mm, is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 5: Preparation of Tin-Containing Molecular Sieves (Tin-Containing Zeolitic Materials Having a BEA Framework Structure) Via Solid-State Ion-Exchange Reference Example 5.1: Tin-Containing Zeolitic Materials Having a BEA Framework Structure Having a Tin Content of 12.4 Weight-%

50.0 g of the deboronated zeolitic material having a BEA framework structure described in Reference Example 5.3.2 below were added to a kneader together with 14.2 g of tin(II) acetate (Sn(OAc)$_2$ [CAS-No: 638-39-1]), and the mixture was first dry-mixed, then the mixture was mashed with 50 ml of de-ionized water using a kneader, and the resulting mixture was kneaded for 15 minutes. After the kneading, the mixture was dried overnight at 60° C. Subsequently, the dried mixture was heated to a temperature of 500° C. under nitrogen (heating ramp: 2 K/min) and kept at 500° C. for 3 h, followed by calcination at 500° C. for 3 h under air. The obtained powder material had a Sn content of 12.4 weight-%, a silicon (Si) content of 35 weight-%, a B content of less than 0.03 weight-%, and a TOC of less than 0.1 weight-%. The BET specific surface area measured by DIN 66131 was 443 m$^2$/g, the crystallinity was 45% determined by XRD, and the water uptake was 12 weight-%.

Reference Example 5.2: Tin-Containing Zeolitic Materials Having a BEA Framework Structure Having a Tin Content of 1.1 Weight-%

5.2.1 Preparing a Boron-Containing Zeolitic Material Having a BEA Framework Structure 259 g de-ionized water were provided in a vessel. Under stirring at 120 rpm (rounds per minute), 440 g tetraethylammonium hydroxide were added and the suspension was stirred for 10 minutes at room temperature. Thereafter, 75.6 g boric acid were suspended and the suspension was stirred for another 30 minutes at room temperature. Subsequently, 687.9 g Ludox® AS-40 were added, and the resulting mixture was stirred for another hour at room temperature. The finally obtained mixture was transferred to a crystallization vessel and heated to 160° C. and stirred at 140 rpm for 120 h. The mixture was cooled to room temperature and subsequently. De-ionized water (twice the amount of the mixture) was added, resulting in a mixture having a pH of 10.0. This mixture was adjusted to a pH of 7-8 by adding aqueous HNO$_3$ (10 weight-% HNO$_3$). The mixture was subjected to filtration and the filter cake was washed with de-ionized water until the washing water had a conductivity of less than 150 microSiemens. The thus obtained filter cake was subjected to drying at 120° C. for 2 h under air, followed by calcination at 490° C. for 5 h under air (heating ramp: 2 K/min). The calcined material had a B content of 0.89 weight-%, a Si content of 47 weight-%, a total carbon content of (TOC) of less than 0.1 weight-%, a crystallinity determined by XRD of 42%, and a BET specific surface area determined by DIN 66131 of 257 m$^2$/g.

5.2.2 Deboronation and Forming Vacant Tetrahedral Sites 2,100 g de-ionized water were passed in a 4 l stirred vessel. Under stirring, 140 g of the material obtained from Reference Example 5.2.1 above were added, and the resulting mixture heated to 100° C. The mixture was kept at this temperature under reflux for 10 h. Then, the mixture was cooled to room temperature. The cooled mixture was subjected to filtration and the filter cake was washed with de-ionized water. The thus obtained filter cake was subjected to drying at 120° C. for 12 h under air (heating ramp: 3 K/min), followed by calcination at 550° C. for 5 h under air (heating ramp: 2 K/min). The calcined material had a B content of 0.15 weight-%, a Si content of 49 weight-%, a total carbon content of (TOC) of less than 0.1 weight-%.

5.2.3 Incorporating Tin Via Solid-State Ion-Exchange 25 g of the deboronated zeolitic material having a BEA framework structure described in Reference Example 5.2.2 above were added to a mixer (mill type Microton MB550) together with 1.02 g of tin(II) acetate (Sn(OAc)$_2$ [CAS-No: 638-39-1]), and the mixture was milled for 15 minutes with 14,000 r.p.m. (rounds per minute). After the milling, the mixture was transferred to a porcelain basket and calcined in air at 500° C. for 3 h under N$_2$ followed by 3 h under air, with a heating ramp of 2 K/min. The obtained powder material had a Sn content of 1.1 weight-%, a silicon (Si) content of 47 weight-%, a B content of less than 0.1 weight-%, and a TOC of less than 0.1 weight-%. The BET specific surface area measured by DIN 66131 was 170 m$^2$/g.

Reference Example 5.3: Tin-Containing Zeolitic Materials Having a BEA Framework Structure Having a Tin Content of 13.1 Weight-%

5.3.1 Preparing a Boron-Containing Zeolitic Material Having a BEA Framework Structure 209 kg de-ionized water were provided in a vessel. Under stirring at 120 rpm (rounds per minute), 355 kg tetraethylammonium hydroxide were added and the suspension was stirred for 10 minutes at room temperature. Thereafter, 61 kg boric acid were suspended in the water and the suspension was stirred for another 30 minutes at room temperature. Subsequently, 555 kg Ludox® AS-40 were added, and the resulting mixture was stirred at 70 rpm for another hour at room temperature. The liquid gel had a pH of 11.8 as determined via measurement with a pH electrode. The finally obtained mixture was transferred to a crystallization vessel and heated to 160° C. within 6 h under a pressure of 7.2 bar and under stirring (140 rpm). Subsequently, the mixture was cooled to room temperature. The mixture was again heated to 160° C. within 6 h and stirred at 140 rpm for additional 55 h. The mixture was cooled to room temperature and subsequently, the mixture was heated for additional 45 h at a temperature of 160° C. under stirring at 140 rpm. 7800 kg de ionized water were added to 380 kg of this suspension. The suspension was stirred at 70 rpm and 100 kg of a 10 weight-% $HNO_3$ aqueous solution was added. From this suspension the boron containing zeolitic material having a BEA framework structure was separated by filtration. The filter cake was then washed with de-ionized water at room temperature until the washing water had a conductivity of less than 150 microSiemens/cm. The thus obtained filter cake was subjected to pre-drying in a nitrogen stream. The thus obtained zeolitic material was subjected, after having prepared an aqueous suspension having a solids content of 15 weight-%, based on the total weight of the suspension, using de-ionized water, to spray-drying in a spray-tower with the following spray-drying conditions:
drying gas, nozzle gas: technical nitrogen
temperature drying gas:
    temperature spray tower (in): 235° C.
    temperature spray tower (out): 140° C.
nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower—filter—scrubber
gas flow: 1,500 kg/h
filter material: Nomex® needle-felt 20 $m^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 500° C. for 5 h. The calcined material had a $B_2O_3$:$SiO_2$ molar ratio of 0.045, a total carbon content of (TOC) 0.08 weight-%, a crystallinity determined by XRD of 56%, and a BET specific surface area determined by DIN 66131 of 498 $m^2$/g.

5.3.2 Deboronation and Forming Vacant Tetrahedral Sites 840 kg de-ionized water were provided in a vessel equipped with a reflux condenser. Under stirring at 40 rpm, 28 kg of the spray-dried and calcined zeolitic material described above in 5.1 were employed. Subsequently, the vessel was closed and the reflux condenser put into operation. The stirring rate was increased to 70 rpm. Under stirring at 70 rpm, the content of the vessel was heated to 100° C. within 1 h and kept at this temperature for 20 h. Then, the content of the vessel was cooled to a temperature of less than 50° C. The resulting deboronated zeolitic material having a BEA framework structure was separated from the suspension by filtration under a nitrogen pressure of 2.5 bar and washed four times with deionized water at room temperature. After the filtration, the filter cake was dried in a nitrogen stream for 6 h. The obtained deboronated zeolitic material was subjected, after having re-suspended the zeolitic material in de-ionized water, to spray-drying under the conditions as described in 5.3.1. The solid content of the aqueous suspension was 15 weight-%, based on the total weight of the suspension. The obtained zeolitic material had a $B_2O_3$:$SiO_2$ molar ratio of less than 0.002, a water uptake of 15 weight-%, a crystallinity determined by XRD of 48% and a BET specific surface area determined by DIN 66131 of 489 $m^2$/g.

5.3.3 Incorporating Tin Via Solid-State Ion-Exchange 50 g of the deboronated zeolitic material having a BEA framework structure described in Reference Example 5, section 5.3.2, were added to a mixer (mill type Microton MB550) together with 14.2 g of tin(II) acetate ($Sn(OAc)_2$ [CAS-No: 638-39-1]), and the mixture was milled for 15 minutes with 14,000 r.p.m. (rounds per minute). After the milling, the mixture was transferred to a porcelain basket and calcined in air at 500° C. for 3 h under $N_2$ followed by 3 h under air, with a heating ramp of 2 K/min. The obtained powder material had a Sn content of 13.1 weight-%, a silicon (Si) content of 38 weight-%, and a TOC of less than 0.1 weight-%. The BET specific surface area measured by DIN 66131 was 442 $m^2$/g, the crystallinity determined by XRD was 44%, and the water uptake was 11.5 weight-%. The UV/Vis spectrum showed two maxima, one at wavelength of 200 nm with a shoulder around 250 nm. In the FT-IR spectrum the intensity ratio between a first adsorption band with a maximum between 3701 to 3741 $cm^{-1}$ and a second adsorption with the maximum between 3600 to 3690 $cm^{-1}$ was 1.62.

Reference Example 5.4: Tin-Containing Zeolitic Materials Having a BEA Framework Structure Having a Tin Content of 12.0 Weight-%

50 g of the deboronated zeolitic material having a BEA framework structure described in Reference Example 5.3.2 above were added to a mixer (mill type Microton MB550) together with 14.2 g of tin(II) acetate ($Sn(OAc)_2$ [CAS-Nr: 638-39-1]), and the mixture was milled for 15 minutes with 14,000 r.p.m. (rounds per minute). After the milling, the mixture was transferred to a porcelain basket and calcined in air at 500° C. for 3 h, with a heating ramp of 2 K/min.

The obtained powder material had a Sn content of 12.0 weight-%, a silicon (Si) content of 35 wt. % and a TOC of less than 0.1 weight-%. The BET specific surface area measured by DIN 66131 was 391 $m^2$/g, the crystallinity determined by XRD 44%, and the water uptake 15 weight-%. The UV/Vs spectrum showed two maxima, one at wavelength of 200 nm with a shoulder around 250 nm. In the FT-IR spectrum the intensity ratio between a first adsorption band with a maximum between 3701 to 3741 $cm^{-1}$ and a second adsorption with the maximum between 3600 to 3690 $cm^{-1}$ was 1.32.

Reference Example 5.5: Tin-Containing Zeolitic Materials Having a BEA Framework Structure Having a Tin Content of 12.4 Weight-%

50 g of the deboronated zeolitic material having a BEA framework structure described in Reference Example 5.3.2 above were added to a ball mill (17 balls with a total weight of 904 g) placed in an oven, together with 14.2 g of tin(II) acetate (Sn(OAc)$_2$ [CAS-No: 638-39-1]), and the mixture was ball-milled for 15 minutes at 80 r.p.m. After the ball-milling, the mixture heated in said oven to a temperature of 500° C. at a heating ramp of 2 K/min and kept at 500° C. for 3 h.

The obtained powder material had a Sn content of 12.4 weight-%, a silicon (Si) content of 35.5 wt. %, a B content of less than 0.03 weight-%, and a TOC of 0.01 weight-%. The BET specific surface area measured by DIN 66131 was 426 m$^2$/g.

Example 1: Baeyer-Villiger Oxidation of Citral (Compound of Formula (I)) with Hydrogen Peroxide in Tert-Butanol as Solvent Using a Zeolitic Material Having a BEA Framework Structure and a Tin Loading of 12.4 Weight-%

A 1 L glass flask was charged with citral (122.5 g) as indicated in Table 1 below, the zeolitic material according to Reference Example 5. 1 above (8.75 g, Sn loading=12.4 weight-%) and tert-butanol (367.5 g) and heated to 65° C. An aqueous solution of hydrogen peroxide 70 w/w %, 29.75 g) was then added and the reaction mixture was stirred. After cooling to room temperature, the resulting solution was filtered and the filtrate was analyzed by GC using dioxane as internal standard.

The results are shown in Table 1 below.

TABLE 1

Results of Example 1

| Example (E) and Comparative Example (CE)/# | Reaction Time/ min | Citral Type/ % trans-citral | Citral Conversion/% | Selectivity[1] based on hydrogen peroxide/% | Selectivity[2] based on citral/% |
|---|---|---|---|---|---|
| CE1.1 | 55 | 50 | 25 | 46 | 68 |
| CE1.2 | 30 | 7 | 18 | 51 | 50 |
| CE1.3 | 40 | 7 | 22 | 48 | 45 |
| CE1.4 | 50 | 7 | 24 | 45 | 44 |
| CE1.5 | 60 | 7 | 27 | 43 | 47 |
| E1.1 | 3 | 98 | 11 | 80 | 99 |
| E1.2 | 6 | 98 | 20 | 71 | 88 |
| E1.3 | 10 | 98 | 28 | 67 | 78 |
| E1.4 | 15 | 98 | 33 | 67 | 77 |

[1] molar amount of melonal (compound of formula III)) + molar amount of enol formate (compound of formula (II)) obtained from the reaction divided by the molar amount of hydrogen peroxide employed in the reaction
[2] molar amount of melonal (compound of formula III)) + molar amount of enol formate (compound of formula (II)) obtained from the reaction divided by the molar amount of citral (compound of formula (I)) employed in the reaction Results of Example 1

Example 1 clearly shows that when using the compound of formula (I) with a content of the compound of formula (Ia) of more than 50%, both the selectivity based on hydrogen peroxide and the selectivity based on the compound of formula (I) were significantly increased and the conversion of the compound of formula (I) remained in the range of the comparative examples where the compound of formula (I) was employed either with a content of the compound of formula (Ia) of more 50% or less than 50%.

With respect to Example E1.1, it is noted that while the conversion of the compound of formula (I) was lower than the conversions of the Comparative Examples, the selectivities exhibited by far the highest values; in particular, it is noted that it is these selectivity values which represent a decisive parameter for the industrial application of a reaction.

Example 2: Baeyer-Villiger Oxidation of Trans-Citral (Compound of Formula (Ia)) with Hydrogen Peroxide in Methyl Tert-Butyl Ether as Solvent Using Different Tin-Containing Zeolitic Materials Having a BEA Framework Structure For each run catalyst, a 1 L glass flask was charged with 122.5 g citral (compound of formula (I)), having a content of trans-citral (compound of formula (Ia)) of 98%), a catalyst as indicated in Table 2 below, and methyl tert-butyl ether a solvent, and heated to 50° C. An aqueous solution of hydrogen peroxide (70 w/w %,) was then added so that in the mixture, 1.3 molar equivalents of the compound of formula (Ia) relative to hydrogen peroxide were present. The amount of catalyst was, in each experiment, 6.6 weight-% relative to the compound of formula (I). The reaction mixture stirred, and the reaction was carried out for 150 min in each experiment. After cooling down to room temperature, the solution was filtered and the filtrate was analyzed by GC using dioxane as internal standard.

The results are shown in Table 2 below.

TABLE 2

Results of Example 2

| Example (E)/# | Sn Content of catalyst/ weight % | Catalyst from Reference Example/# | Citral Conversion/% | Selectivity to melonal[1] based on citral/% |
|---|---|---|---|---|
| E2.1 | 1.1 | 5.2 | 11 | 63 |
| E2.2 | 13.1 | 5.3 | 18 | 66 |
| E2.3 | 12.7 | 5.4 | 10 | 73 |
| E2.4 | 12.4 | 5.5 | 22 | 55 |

[1] molar amount of melonal (compound of formula III)) + molar amount of enol formate (compound of formula (II)) obtained from the reaction divided by the molar amount of citral (compound of formula (I)) employed in the reaction Results of Example 2

Example 2 shows that all tin-containing molecular sieves employed in the Baeyer-Villiger oxidation which were prepared according to simple methods avoiding the disadvantages of the preparation process according to Corma et al., Journal of Catalysis 234 (2005) 96-100 lead to advantageous selectivities to the valuable product melonal. It has to be noted that although some selectivity values according to Table may appear to be lower than some selective values according to Table 1, the selectivity values of Tables 1 and 2 cannot be compared with each other because different solvents and different catalysts at different process conditions are used. While Example 1 allows a direct comparison and thus illustrates the advantage of the use of the trans-form of citral as starting material compared to the use of the 1:1 mixture taught in the art, Example 2 shows the general validity of the inventive concept illustrated by a variety of catalysts.

CITED LITERATURE

Corma et al., Journal of Catalysis 234 (2005) 96-100
WO 2014/068134 A
Baerlocher et al., Atlas of Zeolite Framework Structures, Sixth Revised Edition, Elsevier, Amsterdam (2007) pp 72-73
K. S. W. Sing, D. H. Everett, R. A. W. Haul, L. Moscou, R. A. Plerotti, J. Rouquerol, T. Siemieniewska, Reporting Physisorption Data for Gas/Solid Systems with Special Reference to the Determination of Surface Area and Porosity (Recommendations 1984) Pure & Appl. Chem. 57 (1985) 603-619

The invention claimed is:

1. A process for preparing a compound of formula (III)

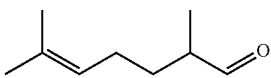

said process comprising
(i) oxidizing a compound of formula (I)

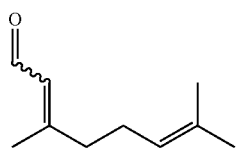

of which more than 50% are present as compound of formula (Ia)

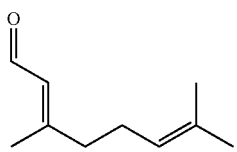

with hydrogen peroxide in the presence of a catalyst comprising a tin-containing molecular sieve, obtaining a reaction mixture comprising a compound of formula (II)

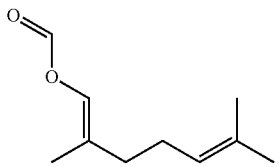

and optionally the compound of formula (III);
wherein the process further comprises
(ii) optionally separating the catalyst comprising a tin-containing molecular sieve, from the mixture obtained from (i);
(iii) hydrolyzing the compound of formula (II), obtaining a mixture containing compound of formula (III);
(iv) optionally separating the compound of formula (III) from the mixture obtained from (iii).

2. The process of claim 1, wherein in (i), at least 95% of the compound of formula (I) are present as compound of formula (Ia).

3. The process of claim 1, wherein in (i), the tin-containing molecular sieve is a tin-containing zeolitic material.

4. The process of claim 1, wherein the tin-containing molecular sieve has a tin content in the range of from 0.1 to 20 weight-%, based on the total weight of the tin-containing molecular sieve.

5. The process of claim 1, wherein in (i), the hydrogen peroxide is employed as an aqueous solution containing hydrogen peroxide in an amount in the range of from 25 to 85 weight-%, based on the total weight of the aqueous solution.

6. The process of claim 1, wherein at the beginning of the oxidation in (i), the molar ratio of the compound of formula (I) relative to the hydrogen peroxide is in the range of from 10:1 to 1:1.

7. The process of any claim 1, wherein the oxidizing in (i) is carried out in a solvent.

8. The process of claim 7, wherein the solvent comprises one or more alcohols.

9. The process of claim 7, wherein at the beginning of the oxidizing in (i), the weight ratio of the compound of formula (I) relative to the solvent in the range of from 1:10 to 1:2.

10. The process of claim 1, wherein the oxidizing in (i) is carried out at temperature of the reaction mixture in the range of from 30 to 90° C.

11. The process of claim 1, wherein in (iii), the hydrolyzing is carried out by adding an aqueous base to the reaction mixture obtained from the oxidizing in (i), optionally after separating in (ii), obtaining an organic phase containing the compound of formula (III) and an aqueous phase and wherein in (iv), the separating of the compound of formula (III) from the mixture obtained from (iii) comprises separating the organic phase from the aqueous phase, and wherein the compound of formula (III) is separated from the organic phase.

12. A mixture comprising a compound of formula (I)

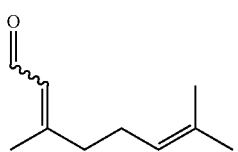

wherein more than 50% of the compound of formula (I) are present as compound of formula (Ia)

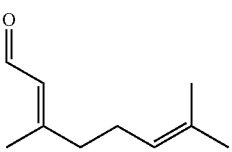

and a catalyst comprising a tin-containing molecular sieve.

13. A method comprising increasing the selectivity and/or decreasing the reaction time of the Baeyer-Villiger oxidation of the compound of formula (I)

for preparing a compound of formula (III)

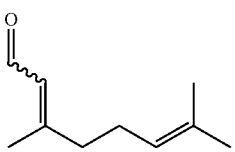
(I)

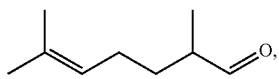
(III)

compared to the respective Baeyer-Villiger oxidation of the compound of formula (I) of which at most 50% are present as compound of formula (Ia)

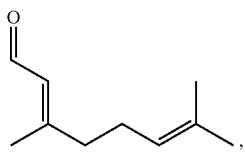
(Ia)

at otherwise identical oxidation conditions, the method comprising oxidizing
a compound of formula (I)
of which more than 50% are present as compound of formula (Ia)
to prepare a compound of formula (III).

14. The process of claim 1, wherein in (i), the tin-containing molecular sieve is a tin-containing zeolitic material, wherein the framework structure type of the tin-containing zeolitic material selected from the group consisting of BEA, MWW, MFI, a mixture of two or more thereof, and a mixed type of two or more thereof.

15. The process of claim 1, wherein the tin-containing molecular sieve has a tin content in the range of from 2 to 14 weight-%, based on the total weight of the tin-containing molecular sieve.

16. The process of claim 1, wherein in (i), the hydrogen peroxide is employed as an aqueous solution containing hydrogen peroxide in an amount in the range of from 65 to 75 weight-%, based on the total weight of the aqueous solution.

17. The process of claim 1, wherein at the beginning of the oxidation in (i), the molar ratio of the compound of formula (I) relative to the hydrogen peroxide is in the range of from 5:1 to 1:1.

18. The process of claim 7, wherein the solvent one or more of tert-butanol, 2-methyl-2-butanol, n-pentanol, 3-methyl-1-butanol, n-hexanol, 2-methyl-1-pentanol, 3-heptanol, 2-ethyl-1-hexanol, 2-octanol, 1-octanol, 2,4,4-trimethyl-1-hexanol, 2,6-dimethyl-4-heptanol, 2-propyl-1-heptanol, and 2-propyl-5-methyl-1-hexanol, or wherein the solvent comprises one or more ethers.

* * * * *